(12) United States Patent
Globerman et al.

(10) Patent No.: US 7,097,648 B1
(45) Date of Patent: Aug. 29, 2006

(54) EXPANDABLE ELEMENT DELIVERY SYSTEM

(75) Inventors: Oren Globerman, Kfar-Shmaryahu (IL); Ronen Shavit, Tel-Aviv (IL); Boaz Shenhav, Herzelia (IL)

(73) Assignee: Disc-O-Tech Medical Technologies Ltd., Herzelia (IL)

( * ) Notice: Subject to any disclaimer, the term of this patent is extended or adjusted under 35 U.S.C. 154(b) by 0 days.

(21) Appl. No.: 09/890,318

(22) PCT Filed: Jan. 27, 2000

(86) PCT No.: PCT/IL00/00056

§ 371 (c)(1),
(2), (4) Date: Jul. 25, 2001

(87) PCT Pub. No.: WO00/44321

PCT Pub. Date: Aug. 3, 2000

(30) Foreign Application Priority Data

Jan. 27, 1999 (IL) .................................. 128261

(51) Int. Cl.
 *A61F 2/46* (2006.01)

(52) U.S. Cl. .............................. 606/99; 606/61; 606/86; 623/17.16; 623/17.11

(58) Field of Classification Search ................... 606/99, 606/53, 90, 97, 86, 80, 61; 623/17.16, 17.11, 623/16.11, 11.11
See application file for complete search history.

(56) References Cited

U.S. PATENT DOCUMENTS

| 817,793 | A | 4/1906 | Hausmann |
|---|---|---|---|
| 3,108,593 | A | 10/1963 | Glassman |
| 3,846,846 | A | 11/1974 | Fischer et al. |
| 3,867,728 | A | 2/1975 | Stubstad et al. |
| 4,204,531 | A | 5/1980 | Aginsky |
| 4,274,163 | A | 6/1981 | Malcom et al. |
| 4,346,708 | A | 8/1982 | LeVeen et al. |
| 4,475,856 | A | 10/1984 | Toomingas |
| 4,632,101 | A | 12/1986 | Freedland |
| 4,772,287 | A | 9/1988 | Ray et al. |
| 4,854,312 | A | 8/1989 | Raftopoulos et al. |
| 4,904,260 | A | 2/1990 | Ray et al. |
| 4,973,301 | A | 11/1990 | Nissenkorn |
| 4,995,868 | A | 2/1991 | Brazier |

(Continued)

FOREIGN PATENT DOCUMENTS

| DE | 1 810 799 | 6/1970 |
|---|---|---|
| DE | 87 16 073 | 3/1988 |
| DE | 196 12 276 | 10/1997 |

(Continued)

OTHER PUBLICATIONS

Narushima, M.; JP 08–322848; Dec. 10, 1996 & Database WPI; Section PQ; Week 199708; Derwent Publications Ltd., London, GB; Class P31, AN 1997–081321; XP002154628.
Weissman, S.L. et al.; "Trochanteric Fractures of the Femur—Treatment with a Strong Nail and Early Weight–bearing;" Nov.–Dec. 1969; pp. 143–150; Clinical Orthopedics and Related Research; No. 67; XP000964714.

*Primary Examiner*—Pedro Philogene
(74) *Attorney, Agent, or Firm*—Fenster & Company

(57) ABSTRACT

Apparatus for controlling the deformation of an implant during deployment thereof, comprising: a force application mechanism for applying deformation force to the implant, by motion of a force applicator against the implant; and a restraint element positioning mechanism that positions a restraining element such that the deformation of the implant is controlled by restraint of the restraining element on allowable deformation; and a synchronizer that synchronizes the motion of the restraining element and the force applicator, to achieve a desired deformation of the implanted.

163 Claims, 26 Drawing Sheets

U.S. PATENT DOCUMENTS

| | | | |
|---|---|---|---|
| 5,059,193 A | 10/1991 | Kulisch | |
| 5,059,199 A | * 10/1991 | Okada et al. | 606/127 |
| 5,074,871 A | 12/1991 | Groshong | |
| 5,108,404 A | 4/1992 | Scholten et al. | |
| 5,123,926 A | 6/1992 | Pisharodi | |
| 5,171,248 A | 12/1992 | Ellis | |
| 5,171,278 A | 12/1992 | Pisharodi | |
| 5,356,382 A | 10/1994 | Picha et al. | |
| 5,376,123 A | 12/1994 | Klaue et al. | |
| 5,390,683 A | 2/1995 | Pisharodi | |
| 5,423,850 A | 6/1995 | Berger | |
| 5,454,365 A | * 10/1995 | Bonutti | 600/204 |
| 5,480,400 A | 1/1996 | Berger | |
| 5,518,498 A | 5/1996 | Lindenberg et al. | |
| 5,554,101 A | 9/1996 | Matula et al. | |
| 5,578,035 A | 11/1996 | Lin | |
| 5,601,557 A | 2/1997 | Hayhurst | |
| 5,609,637 A | * 3/1997 | Biedermann et al. | |
| 5,637,097 A | 6/1997 | Yoon | |
| 5,658,310 A | 8/1997 | Berger | |
| 5,683,451 A | 11/1997 | Lenker et al. | |
| 5,685,826 A | 11/1997 | Bonutti | |
| 5,690,606 A | 11/1997 | Slotman | |
| 5,693,100 A | 12/1997 | Pisharodi | |
| 5,697,977 A | 12/1997 | Pisharodi | |
| 5,707,390 A | 1/1998 | Bonutti | |
| 5,725,341 A | 3/1998 | Hofmeister | |
| 5,752,969 A | 5/1998 | Cunci et al. | |
| 5,755,732 A | 5/1998 | Green et al. | |
| 5,759,186 A | 6/1998 | Bachmann et al. | |
| 5,782,713 A | 7/1998 | Yang | |
| 5,782,747 A | 7/1998 | Zimmon | |
| 5,782,838 A | 7/1998 | Beyar et al. | |
| 5,785,647 A | 7/1998 | Tompkins et al. | |
| 5,800,549 A | 9/1998 | Bao et al. | |
| 5,827,289 A | 10/1998 | Reiley et al. | |
| 5,865,802 A | 2/1999 | Yoon et al. | |
| 5,876,457 A | 3/1999 | Picha et al. | |
| 5,882,340 A | 3/1999 | Yoon | |
| 5,972,015 A | 10/1999 | Scribner et al. | |
| 6,019,789 A | 2/2000 | Dinh et al. | |
| 6,039,761 A | 3/2000 | Li et al. | |
| 6,126,689 A | * 10/2000 | Brett | |
| 6,127,597 A | 10/2000 | Beyar et al. | |
| 6,129,763 A | 10/2000 | Chauvin et al. | |
| 6,146,401 A | 11/2000 | Yoon et al. | |
| 6,149,651 A | 11/2000 | Drewry et al. | |
| 6,149,664 A | 11/2000 | Kurz | |
| 6,187,015 B1 | 2/2001 | Brenneman | |
| 6,190,381 B1 | 2/2001 | Olsen et al. | |
| 6,214,016 B1 | 4/2001 | Williams et al. | |
| 6,214,037 B1 | 4/2001 | Mitchell et al. | |
| 6,217,608 B1 | 4/2001 | Penn et al. | |
| 6,228,068 B1 | 5/2001 | Yoon | |
| 6,228,082 B1 | 5/2001 | Baker et al. | |
| 6,245,101 B1 | 6/2001 | Drasler et al. | |
| 6,248,110 B1 | 6/2001 | Reiley et al. | |
| 6,261,289 B1 | 7/2001 | Levy | |
| 6,325,812 B1 | 12/2001 | Dubrul et al. | |
| 6,350,271 B1 | * 2/2002 | Kurz et al. | 606/159 |
| 6,375,682 B1 | * 4/2002 | Fleischmann et al. | |
| 6,447,478 B1 | 9/2002 | Maynard | |
| 6,500,182 B1 | * 12/2002 | Foster | 606/127 |
| 6,554,833 B1 | 4/2003 | Levy et al. | |
| 6,780,175 B1 | 8/2004 | Sachdeva et al. | |
| 2002/0068975 A1 | 6/2002 | Teitelbum et al. | |
| 2002/0072768 A1 | 6/2002 | Ginn | |
| 2005/0060023 A1 | 3/2005 | Mitchell et al. | |

FOREIGN PATENT DOCUMENTS

| | | |
|---|---|---|
| EP | 0 044 877 | 2/1982 |
| FR | 2 674 119 | 9/1992 |
| FR | 2 712 486 | 5/1995 |
| FR | 2 722 679 | 1/1996 |
| FR | 2 722 679 | 9/1996 |
| WO | WO 92/14423 | 9/1992 |
| WO | WO 96/32899 | 10/1996 |
| WO | WO 98/38918 | 9/1998 |
| WO | WO 99/39661 | 8/1999 |
| WO | WO 99/52446 | 10/1999 |

* cited by examiner

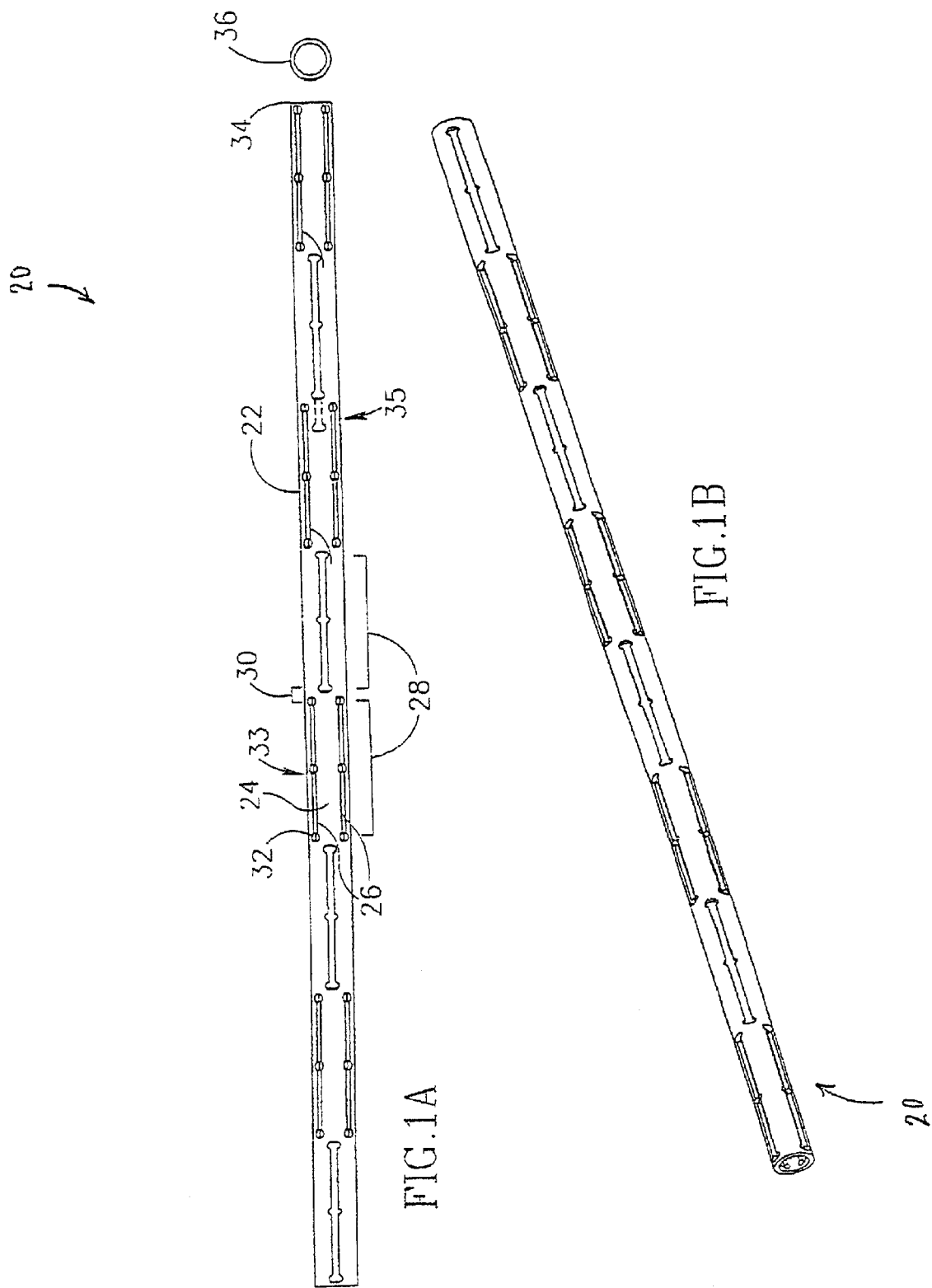

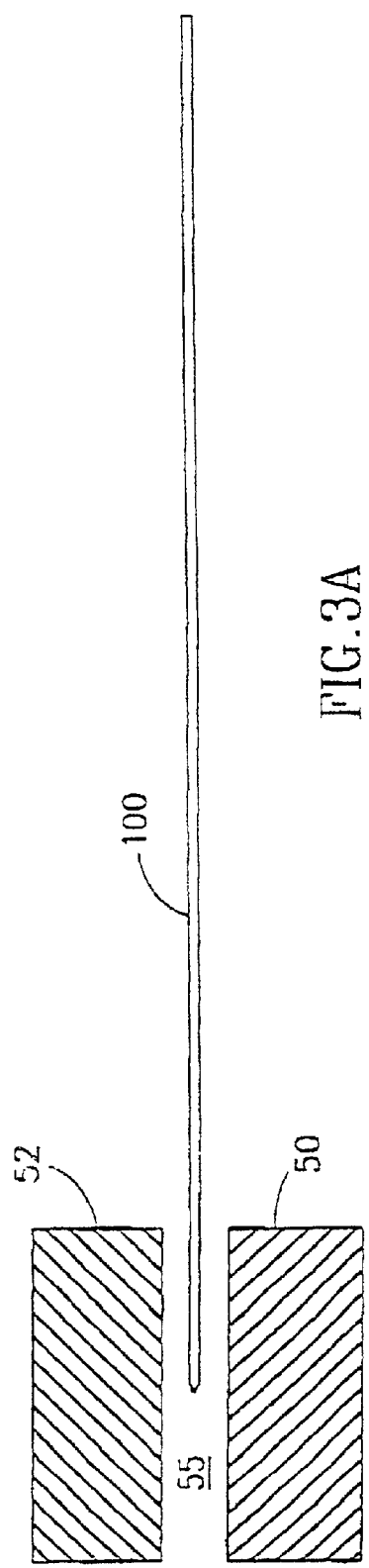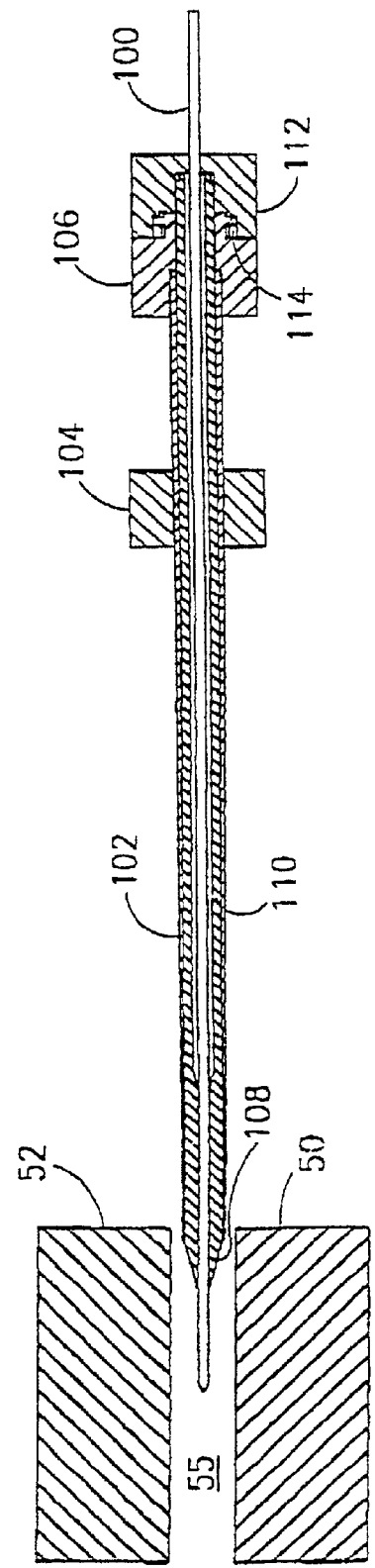

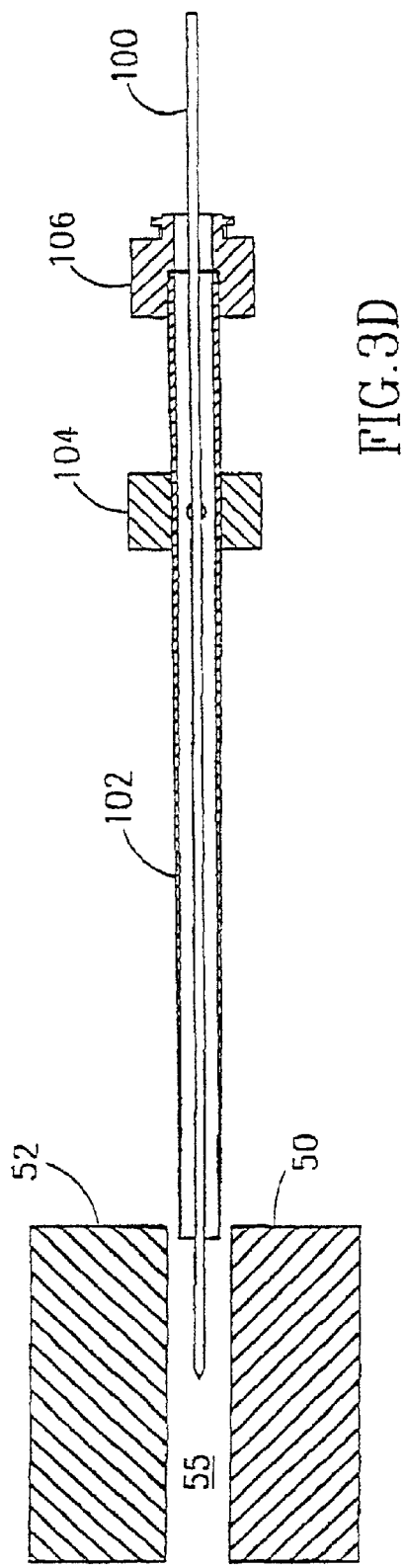
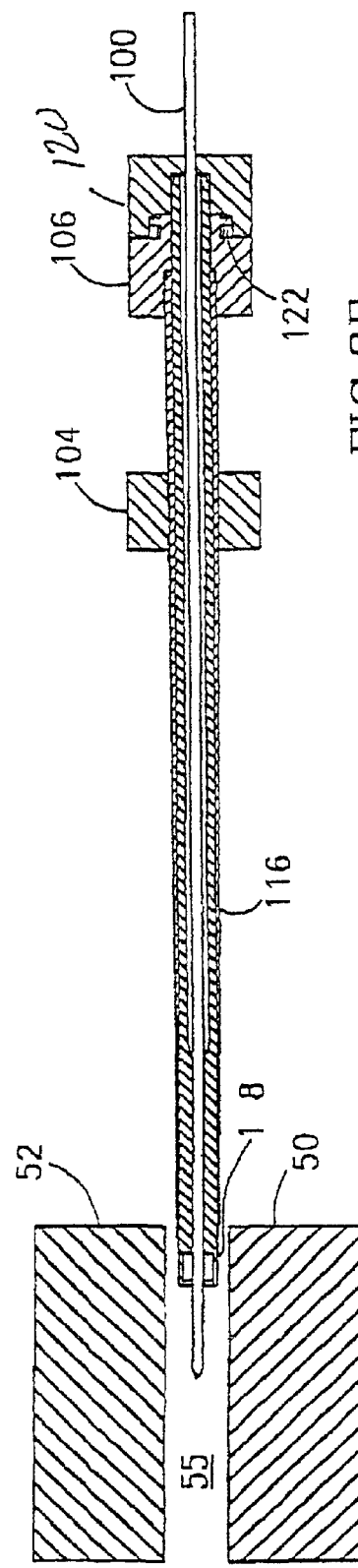
FIG.3D
FIG.3E

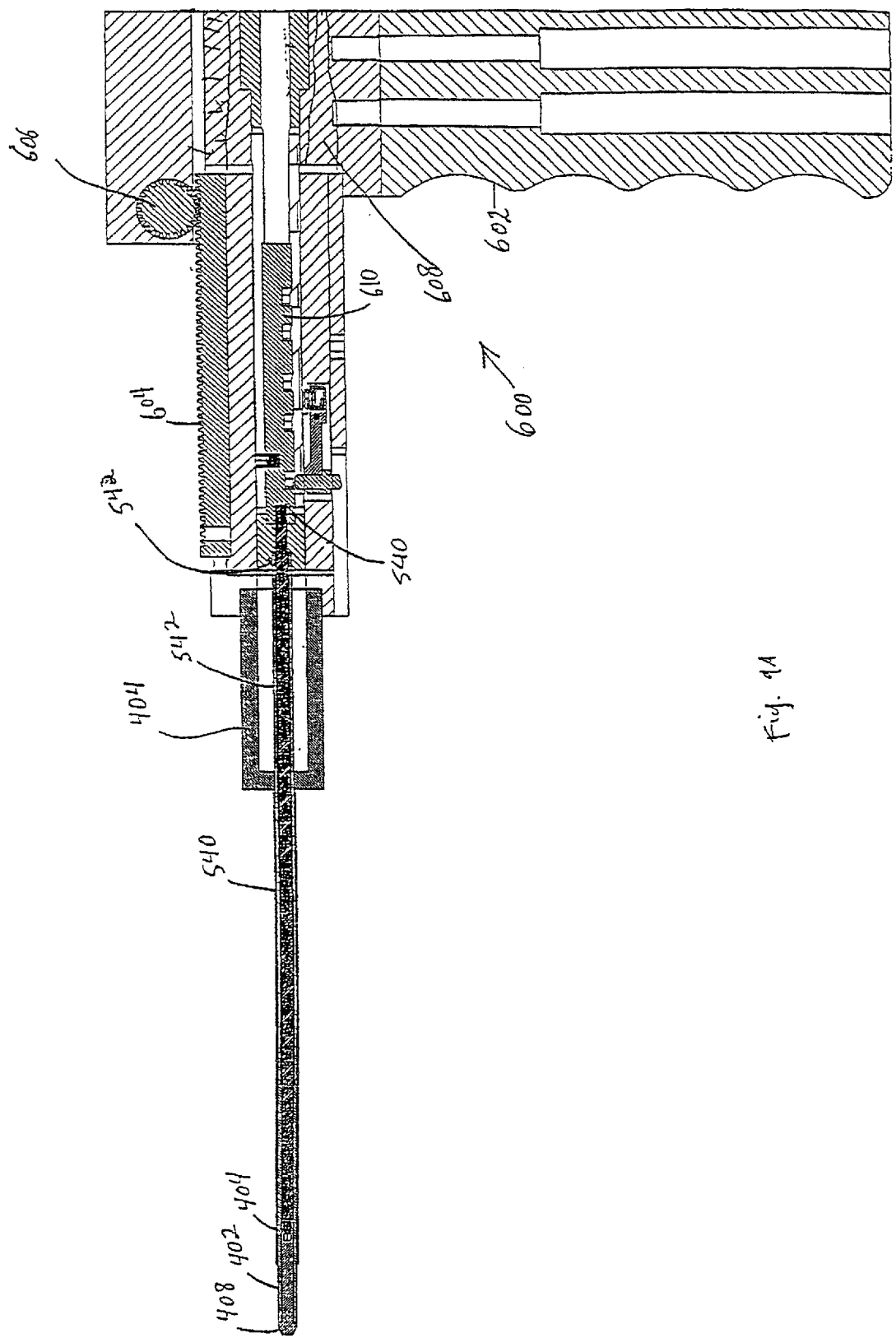

US 7,097,648 B1

EXPANDABLE ELEMENT DELIVERY SYSTEM

RELATED APPLICATIONS

This application is a U.S. national filing of PCT Application No. PCT/IL00/00056, filed Jan. 27, 2000. This application is also related to PCT Application Nos. PCT/IL00/00055 and PCT/IL00/00058, the disclosures of which are incorporated herein by reference.

FIELD OF THE INVENTION

The present invention relates to delivery systems for expandable implants, and especially to delivery systems for a spinal prosthesis.

BACKGROUND OF THE INVENTION

A common medical situation is that of a ruptured spinal disc. Material that exits the disc may press against the spinal cord, causing severe pain. A ruptured disc is typically treated by a surgical procedure, in which the damaged disc is partially or completely removed, and spinal fusion, in which at least the two vertebrae adjacent the removed disc are fused.

Disk removal may be performed percutaneously, for example via a tube through which tissue removal devices and/or an endoscope are provided.

Several approaches exist for spinal fusion. In one approach, the two vertebrae are connected using a plate and/or screws. In another approach, a spacer (also called a "cage device") is inserted between the two vertebrae, so that bone growth into the space will fuse the adjacent vertebra. Typically, the axis of the spacer is perpendicular to the axis of the spine and to the plane of the body. Sometimes the spacer includes a plurality of holes, to encourage bone growth into the spacer. PCT publication WO 98/38918, the disclosure of which is incorporated herein by reference, describes a spacer that is inserted in a collapsed condition and expanded to fill the inter-vertebral space. Another type of spacer, exemplified by U.S. Pat. 5,123,926 (and others) to Pisharodi, the disclosure of which is incorporated herein by reference, functions like a concrete anchoring screw, in that a portion of the spacer, usually a center portion-thereof, expands by a relatively small amount to engage the adjacent vertebrae.

U.S. Pat. 5,800,549, the disclosure of which is incorporated herein by reference, describes a flexible disc replacement that is inserted using a syringe. However, this replacement does not fuse adjacent vertebrae, rather, it is designed to replace the form and function of a removed inter-vertebral disc.

One disadvantage of some of known fusion devices is that a relatively large entry hole in the body is required to insert the device. In some, a regular-sized surgical incision is required. In others, a minimally invasive laproscope-size hole is required, which is still quite large. Often, the spinal processes and/or other spinal structures are damaged by the insertion of the fusion device.

Another disadvantage of some known fusion devices lies in a relative complexity of procedures for delivering the devices.

Another disadvantage of some known fusion devices is a requirement to trade/off the invasiveness of the procedure (e.g., do the spinal processes need to be cut or the abdomen opened) and the surface contact area between the fusion device and the bone. Generally, if the contact surface is small, the fusion device embeds itself in the bone and the spine slowly shrinks.

SUMMARY OF THE INVENTION

An aspect of some preferred embodiments of the invention relates to a method of controlling the deformation of an implant. In a preferred embodiment of the invention, a force is applied to the implant while the expansion of the implant is constrained by an element external to the implant. The expansion force is preferably applied externally to the implant by may be applied by the implant itself, for example if the implant is super-elastically or elastically deformed or is formed of a shape memory material. In a preferred embodiment of the invention, the force is an axially applied fore that axially contacts the implant, causing it to expand or extend elements radially. In a preferred embodiment of the invention, the constraint element is external to the implant and is moved between or during application of the deformation force, to modify the deformation behavior of the implant. In a preferred embodiment of the invention, the external constrained is retracted as the implant is axially contracted. The axial force may be applied by pushing an element towards the implant and/or by pulling the implant towards an element.

An aspect of some preferred embodiments of the invention relates to a device for controlling the deformation of an implant, in which an operator applies continuous motion to a knob or lever. and the device converts the continuous motion into at least two discrete motions. In an exemplary application, one motion is for applying force to the implant for deforming it and one motion is for moving a constraining element that affects the deformation of the implant under the force.

In a preferred embodiment of the invention, an alternating pin mechanism is provided for alternating the applied operator motion between a deformation force providing element and a constraint element.

In an alternative embodiment of the invention, an eccentric-wheel mechanism is provided, which wheel advances and retracts two arms, one arm which applies force to the deformation and one arm which moves the constraining element. Preferably, the two arms alternately active the constraining element and the deformation. In some embodiments, both arms move in phase and in other embodiments the two arms move out of phase or even unsynchronized with regard to cycles.

In a preferred embodiment of the invention, an apertured or nubbed plate is provided for controlling the motions. In a nubbed plate, the nubs are preferably one way nubs, which allow an arm to engage a nub when moving in one direction and slip over the nubs when moving in the other direction. In an apertured plate, a spring loaded pin is preferably provided, for locking into an aperture when a motion is completed and for sliding along the plate when the motion is in progress.

In a preferred embodiment of the invention, the deforming force is applied as axially as possibly with respect to the delivery system, to prevent twisting moments.

In an alternative embodiment, a two-phase apparatus is provided. The apparatus comprises two components, one for applying force to a spacer and one for retracting a collar that acts as a constraining element. In each component, an operator activates the component to apply the desired forces or motion and at the completion of the activation, the component locks. The operator then activates the other component until it locks. Repeats are achieved by unlocking the components and activating them again. In a particular implementation, the collar is advanced when force is applied to the spacer, so that the collar maintains a same position relative to the proximal end of the spacer.

An aspect of some preferred embodiment of the invention relates to a device for intra-vertebral measurement. In a preferred embodiment of the invention, the device comprises a shaft having two wings at its end. When the wings extend, the shaft advances or retracts, the amount of motion of the shaft being determined by the extend of extension of the wings. Various mechanisms may be used for extending the wings. In a preferred embodiment of the invention, the wings form a parallelogram, with the shaft attached to one vertex of the parallelogram and the opposite vertex constrained form moving. Advancing the shaft, extends the wings. One, two or more wings may be provided, thus enabling measurement to one side, a planar measurement or a volume measurement. Alternatively or additionally, a plurality of concentric shafts may be provided, each with its own set of wings. The wings of the different shafts may be perpendicular to each other, or at any other angle, for example parallel to each other. Possibly, the angle between the wings is controlled by rotating the shafts relative to each other.

In some mechanisms, the relation between shaft motion and wing extension is not linear. In a preferred embodiment of the invention, a mechanical display is coupled to the shaft and converts the shaft motion into a more readable scale, such as a linear or quasi linear scale of wing extension.

An aspect of some preferred embodiments of the invention relates to kits for implant procedures, comprising two or more of a delivery system (which may be sterilized or be disposable), an implant, a collar, a bolt, an access tube, a trephine, a guide wire, a vertebra puncher and/or an obturator. Preferably, the kit parts are adapted for a size and access direction of a spacer. In some spacers, the spacer axis when the spacer is expanded is not parallel to the spacer insertion direction. This can be achieved by providing different length spike son either side of the space. Thus, a rectangular spacer, parallel to the abdomen and back can be inserted at an oblique angle to the spine.

There is thus provided in accordance with a preferred embodiment of the invention, apparatus for controlling the deformation of an implant during deployment thereof, comprising:

a force application mechanism for applying deforming force to the implant, by motion of a force applicator against the implant; and a restraint element positioning mechanism that positions a restraining element such that the deformation of the implant is controlled by restraint of the restraining element on allowable deformation; and a synchronizer that synchronizers the motion of the restraining element and the force applicator, to achieve a desired deformation of the implant.

Preferably, the apparatus comprises a force input which receives continuous motion and couples it to the force application mechanism and to the restraint element positioning mechanism. Preferably, said continuous motion is reciprocating motion. Preferably, said restraint positioning mechanism moves said restraint element during one stroke of said reciprocating motion. Preferably, said one stroke comprises a retraction of said restraint mechanism from said implant.

In a preferred embodiment of the invention, said force application mechanism moves said force applicator during one stroke of said reciprocating motion. Preferably, said one stroke comprises a retraction of said force applicator from said implant. Alternatively, said one stroke comprises an advance of said force applicator towards said implant.

In a preferred embodiment of the invention, said force application mechanism comprises a selective coupler that selectively couples said input motion to said force applicator. Alternatively or additionally, said element positioning mechanism comprises a selective coupler that selectively couples said input motion to said restraining element. Alternatively or additionally, said synchronized motion is repetitive, comprises a plurality of cycles of positioning said restraining element and applying said force. Alternatively or additionally, said motion is applied simultaneously to said restraint element positioning mechanism and to said force application mechanism.

In a preferred embodiment of the invention, said motion is applied alternately to said restraint element positioning mechanism and to said force application mechanism. Preferably, the apparatus comprises an alternating locking mechanism that alternately couples the motion form the force input to the restraint element positioning mechanism and to the force application mechanism.

In a preferred embodiment of the invention, said force input comprises a manual force input.

In a preferred embodiment of the invention, said force input comprises a motorized force input.

In a preferred embodiment of the invention, said synchronizer is integrated with said mechanisms. Alternatively or additionally, said synchronizer is manual, providing an indication to an operator to switch between the mechanisms. Alternatively, said synchronizer is automatic, switching by itself between the mechanisms.

In a preferred embodiment of the invention, said synchronizer comprises a pin extractor for decoupling a pin from one mechanism and coupling the pin to another mechanism. Preferably, said synchronizer comprises a spring for urging said pin towards one of said mechanisms and an inclined plane for withdrawing said pin from said one mechanism and urging said pin towards said other mechanism.

In a preferred embodiment of the invention, said synchronizer blocks the motion of one of said mechanisms when a desired motion effect of said mechanism is. achieved. Preferably, the apparatus comprises a pin that engages an aperture to effect said locking.

In a preferred embodiment of the invention, said restraint mechanism comprises an unevenly surfaced element for coupling said motion to said restraint element.

In a preferred embodiment of the invention, said force application mechanism comprises an unevenly surfaced element for coupling said motion to said force applicator. Alternatively or additionally, said unevenly surfaced element comprises a nubbed plate. Preferably, said nubs are one-way nubs that allow an arm element of said mechanisms to slip over them when the arm travels in one direction relative to the nubs and engages the arm when the arm travels in the opposite relative direction.

In a preferred embodiment of the invention, said unevenly surfaced element comprises an apertured plate.

In a preferred embodiment of the invention, said uneven surface comprises even surface portions separated, by uneven surface portions, a plurality of separation distances defined by said separation of surface portions. Preferably, said separation distances determine the deformation of said implant. Alternatively or additionally, said separation distances take into account a plastic deformation of said implant. Alternatively or additionally, said separation distances take into account an elastic deformation of said implant. Alternatively or additionally, wherein said separation distances take into account a spring-back of said implant.

In a preferred embodiment of the invention, said force applicator and said force application mechanism are substantially restricted to a straight, narrow, elongate volume, thereby reducing moments on the force application mechanism. Alternatively or additionally, said force applicator pushes against said implant.

In a preferred embodiment of the invention, said force applicator pulls a base against a far side of said implant.

In a preferred embodiment of the invention, said force applicator exhibits axial motion, along an axis connecting the force applicator and the implant. Alternatively, said force applicator exhibits rotational motion, around an axis connecting the force applicator and the implant. Alternatively, said force applicator exhibits only axial motion, along an axis connecting the force applicator and the implant.

In a preferred embodiment of the invention, said restraint element exhibits axial motion, along an axis connecting the force applicator and the implant.

In a preferred embodiment of the invention, said restraint element exhibits rotational motion, around an axis connecting the force applicator and the implant. Alternatively, said force applicator exhibits only axial motion, during times when force is applied by it to the implant, along an axis connecting the force applicator and the implant.

In a preferred embodiment of the invention, said force applicator applies at least 20 Kg to said implant. Alternatively or additionally, said force applicator applies at least 40 Kg to said implant. Alternatively or additionally, said force applicator applies at least 60 Kg to said implant. Alternatively or additionally, said force applicator applies at least 100 Kg to said implant.

In a preferred embodiment of the invention, said restraint element and said force applicator are elongate elements. Preferably, said restraint element and said force applicator are cylindrical elements.

In a preferred embodiment of the invention, said cylindrical elements are tubes.

In a preferred embodiment of the invention, said force applicator comprises two concentric elements, an outer element which applies force away from said apparatus towards said implant and an inner counter force element that applies force from said implant towards said apparatus. Preferably, said inner element is mechanically coupled to said implant. Alternatively said outer element is mechanically coupled to said implant.

In a preferred embodiment of the invention, said motion of said force applicator comprises motion of only one of said concentric elements relative to said apparatus. Preferably, said inner element retracts towards said apparatus during said motion of said force applicator. Alternatively, said outer element advances away from said apparatus during said motion of said force applicator.

In a preferred embodiment of the invention, said inner element is decoupled from said implant by unscrewing it. Preferably, said inner element extends substantially all the way through said apparatus.

In a preferred embodiment of the invention, the apparatus comprises a handle for holding said apparatus by an operator.

In a preferred embodiment of the invention, the apparatus comprises means for fixing said apparatus to said patient.

In a preferred embodiment of the invention, the apparatus comprises means for fixing said apparatus to a bed on which said patient lies.

In a preferred embodiment of the invention, said synchronizer adapts said apparatus for deforming a particular implant from a set of same types of implants having different geometries.

In a preferred embodiment of the invention, said synchronizer synchronizes said force applicator to apply force to said implant after said implant is completely expanded.

In a preferred embodiment of the invention, said restraint element has an outer diameter of less than 7 mm. Alternatively or additionally, said restraint element has an outer diameter of less than 6 mm. Alternatively or additionally, said restraint element has an outer diameter of less than 5 mm. Alternatively or additionally, said restraint element has an outer diameter of less than 4 mm.

In a preferred embodiment of the invention, said implant is a spinal implant for fusing adjacent vertebrae. Alternatively or additionally, said implant is an axially contracting and radially expanding implant. Alternatively or additionally, said implant comprises a slotted tube, which as it contracts, radially extends a plurality of spikes and wherein said restraining element encloses said tube and prevents the extension of at least one of said spikes.

In a preferred embodiment of the invention, said implant comprises a slotted tube, to which force is applied against an end of said tube, to deform the tube. Alternatively or additionally, said implant radially expands by said deforming at least by a ratio of two. Alternatively or additionally, said implant radially expands by said deforming at least by a ratio of four.

There is also provided in accordance with a preferred embodiment of the invention, a method of controlling the deformation of an implant, comprising:

providing a medical implant;

positioning a restraining element relative to said implant, which restraining element prevents deformation of at least some of said implant;

applying a deformation force to said implant using at least one tube;

controlling the deformation of the implant using the restraining element;

moving said restraining element to a new position; and repeating said applying, said controlling and said moving, a plurality of times. Preferably, said deformation comprises radial expansion. Alternatively or additionally, said restraining element is inside said implant.

Alternatively, said restraining element is outside said implant.

In a preferred embodiment of the invention, said motion of said restraining element is controlled using a mechanism external to the implant. Preferably, said external mechanism receives a continuous motion input from an operator. Preferably, the method comprises converting said continuous motion into discrete motion of said restraining element.

Alternatively or additionally, the method comprises converting said continuous motion into discrete application of force to said implant.

In a preferred embodiment of the invention, said motion and said force application do not overlap in time.

In a preferred embodiment of the invention, said motion and said force application do overlap in time.

There is also provided in accordance with a preferred embodiment of the invention, a method of controlling the deformation of an implant, composing:

providing an axial implant having a plurality of spikes extending radially thereto, arranged along the implant's axis, which implant is in a collapsed state where said spikes do not extend;

enclosing said implant with a collar that restrains the extension of said spikes;

inserting said implant into a desired location;

retracting said collar to allow at least one spike to extend; and repeating said retracting until substantially all of said spikes are extended. Preferably, said spikes extend as a result of forces stored within said implant. Preferably, said implant is formed of a super-elastic material. Alternatively, said implant is formed of a shape-memory material.

In a preferred embodiment of the invention, said spikes extend as a result of forces applied externally to said implant. Preferably, said forces are axially applied to said implant. Preferably, the method comprises applying an axial force to said implant after all of said spikes are extended.

There is also provided in accordance with a preferred embodiment of the invention, a measurement apparatus for taking measurements inside the body, comprising:

a hollow tube, defining at least one slot at its end;

a shaft disposed within said tube; and at least one wing coupled to said shaft and adapted to extend through said slot, wherein an extension position of said wing determines an axial motion of said shaft in said tube, wherein said apparatus is adapted to come in contact with body fluids and wherein said apparatus is sterile. Preferably, said apparatus is sterilizable. Alternatively or additionally, said tube comprises defines at least two slots and wherein said at least one wing comprises at least two wings.

In a preferred embodiment of the invention, extension of said wings retracts said shaft towards said wings.

In a preferred embodiment of the invention, extension of said shaft away from said wings extends said wings.

In a preferred embodiment of the invention, said wings are molded from a single piece of plastic.

In a preferred embodiment of the invention, said at least one wing, defines a parallelogram, with the shaft attached to one vertex of the parallelogram and the two neighboring vertexes of the parallelogram comprises the extended parts of two wings.

In a preferred embodiment of the invention, the apparatus comprises a dial coupled to said shaft and displaying an extension of said wings as a function of a relative displacement between said shaft and said tube. Preferably, said dial comprises a scale converter that converts a non-linear coupling of said wing motion to said shaft motion into a linear scale display.

In a preferred embodiment of the invention, the apparatus comprises an axial position control for controlling an axial position of said tube relative to a body.

BRIEF DESCRIPTION OF THE DRAWINGS

The present invention will be more clearly understood from the following detailed description of the preferred embodiments of the invention and from the attached drawings, in which:

FIG. 1A shows a flat projection of an expandable spacer, in an un-expanded configuration thereof, in accordance with a preferred embodiment of the invention;

FIG. 1B shows a perspective view of the spacer of FIG. 1A;

FIGS. 3A–3F illustrate a method of providing a guide tube into an intra-vertebral space, in accordance with a preferred embodiment of the invention;

FIGS. 9A–9B illustrate a delivery control systems utilizing an alternating pin, in accordance with a preferred embodiment of the invention;

FIGS. 10A–10B illustrate an eccentric-rotation based delivery system, in accordance with a preferred embodiment of the invention.

DETAILED DESCRIPTION OF THE PREFERRED EMBODIMENTS

Basic Spacer (Cage) Description

Figure 1C:
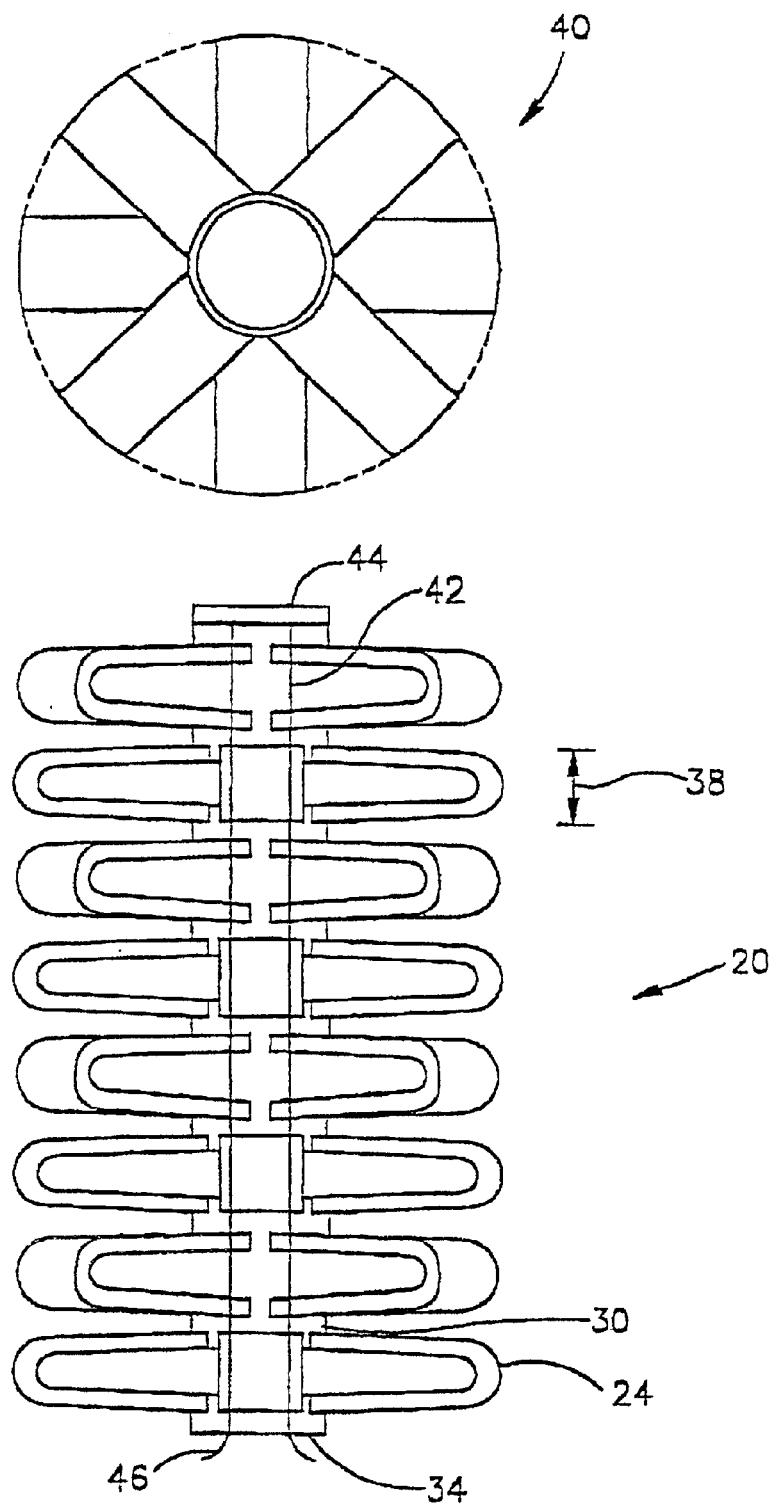
FIG. 1C shows both an axial flat projection and a front flat projection of the spacer of FIG. 1A, in an expanded configuration thereof.

FIG. 1A shows a flat projection of an expandable spacer 20, in an un-expanded configuration thereof, in accordance with a preferred embodiment of the invention. FIG. 1B is a perspective view of spacer 20. Spacer 20 comprises an elongate hollow object 22, such as a tube, having a plurality of spikes 24 defined thereon (in a flattened form), each spike being defined by a pair of slots 26. In a preferred embodiment of the invention, the cross-section of tube 22 is a circle, as shown in an axial projection 36 of the spacer. In the embodiment shown in FIG. 1A, tube 22 includes alternating spike segments 28 and non-spike segments 30. At one end of the tube, an end-cap 34 is preferably defined. In a preferred embodiment of the invention, end-cap 34 is hollow. Alternatively, end-cap 34 is solid, but preferably comprising a porous material or including holes, to enhance bone ingrowth. Alternatively or additionally to end-cap 34, spacer 20 is attached to the end of a tube, such that only a portion of the tube, preferably an end portion, has slits defined therein.

Figure 1D:
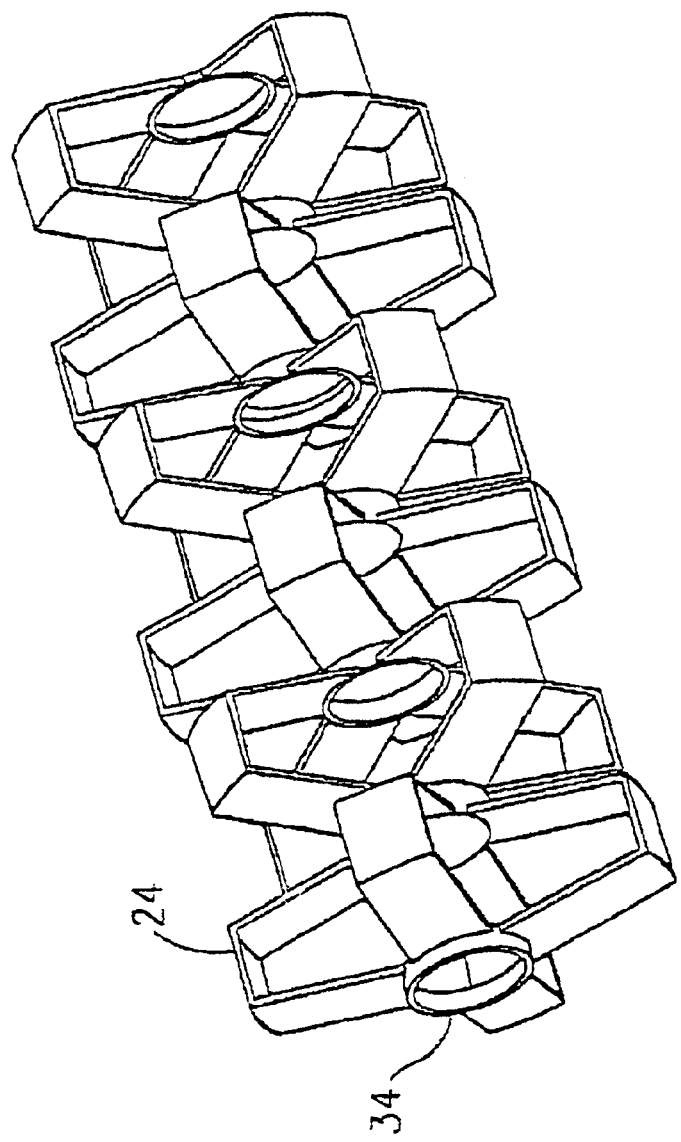
FIG. 1D shows a perspective view of the spacer of FIG. 1A, in an expanded configuration thereof.

FIGS. 1C–1D show spacer 20 in an expanded configuration, FIG. 1C using a flat projection (side and axial) and FIG. 1D using a perspective view. When expanded, spikes 28 extend outwards and tube 22 is axially compressed. Non-spike segments 30 and end-cap(s) 34 preferably do not distort. As can be seen in the figures, a considerable expansion in diameter is achieved, for example a five fold expansion. In addition, a considerable axial contraction is achieved, as evidenced by comparing the thickness of a spike 24 in FIG. 1C (38) with FIG. 1A (28).

In a preferred embodiment of the invention, spacer 20 is maintained in an expanded configuration using a bolt 42. A base 44 of bolt 42 engages one end-cap of spacer 20 and a flared lip 46 (flared for example by an advancing pole element after the spacer is expanded) engages end-cap 34.

Although spacer 20 has been described as including non-spike portions, it should be appreciated that in some preferred embodiments of the invention no such non-spike portions are defined, for example, if the slits are interleaved, as shown by the example of a dotted line 35 in FIG. 1A.

In a preferred embodiment of the invention, tube slits 26 include round holes, for example holes 32, at their ends. Preferably, these holes are defined to reduce the propagation of stress and/or mechanical failure in tube 22. Alternatively or additionally, these holes are defined to weaken the end of the slit so that when spacer 20 is axially collapsed, spikes 28 will preferentially fold out at the ends of the slits (at holes 33). Alternatively or additionally, slits 26 may include holes 33 at their center (the apex of spikes 28), to encourage folding of the spike at the location of the hole.

The above is a description of a limited subset of spacers, further variations are defined in a PCT application filed on even date with the present application in the Israel receiving office and titled "Expandable Element", attorney docket 100/01325, the disclosure of which is incorporated herein by reference.

Basic Delivery Method

Figure 2A:
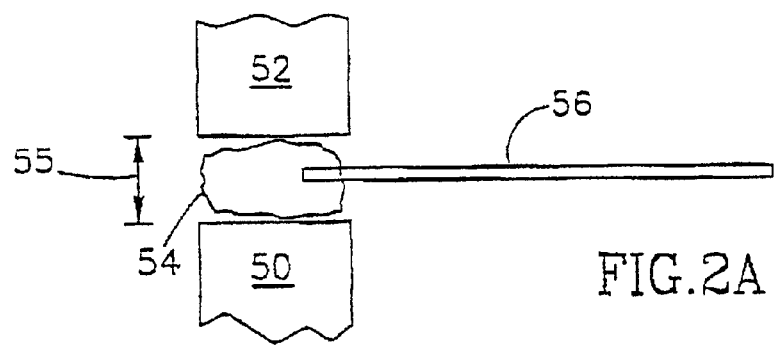
FIGS. 2A–2D illustrate a process of inserting and expanding a spacer, in accordance with a preferred embodiment of the invention.

FIGS. 2A–D illustrate a process of inserting and expanding spacer 20. In FIG. 2A, a damaged disc 54 is located in an inter-vertebral space 55, between a vertebra 50 and a vertebra 52. Typically, but not necessarily, before inserting a spacer between the two vertebra, disc 54 is partially or completely removed. Preferably, disc 54 is removed using a minimally invasive technique, illustrated by a thin needle 56, for example a laproscopic approach, such as described in WO 98/38918.

Figure 2B:
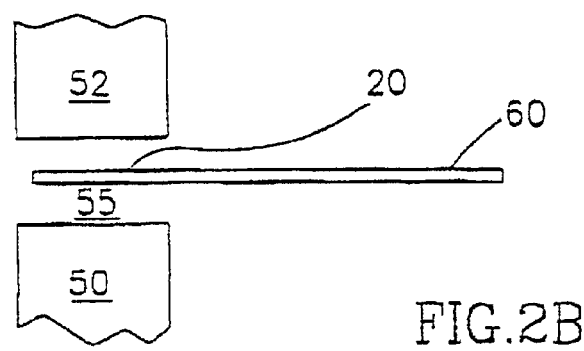

In FIG. 2B, the disc has been removed and a spacer 20 is inserted into inter-vertebral space 55, in an un-expanded configuration. In a preferred embodiment of the invention, spacer 20 is mounted on- or formed at- the end of an elongate member 60. Preferably, spacer 20 is inserted via a syringe or in an "over-tube" which may be retrieved, once the spacer is inserted. Alternatively or additionally, spacer 20 is inserted using X-Ray guidance, to avoid damaging the spinal cord and/or nearby blood vessels.

Figure 2C:
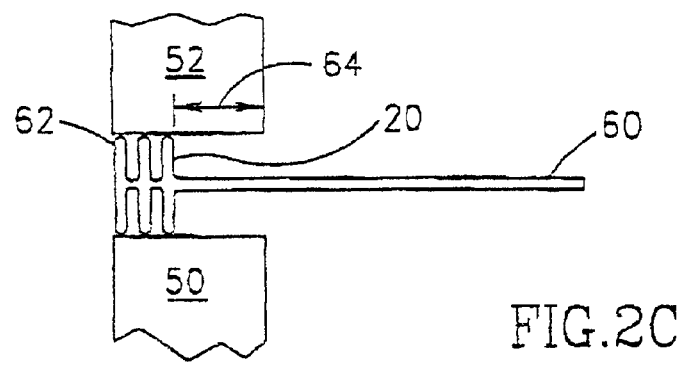

In FIG. 2C, spacer 20 is in the process of being radially expanded (and axially shortened). A portion 62 of spacer 20 is expanded, while a portion 64 of spacer 62 is not yet expanded.

Figure 2D:
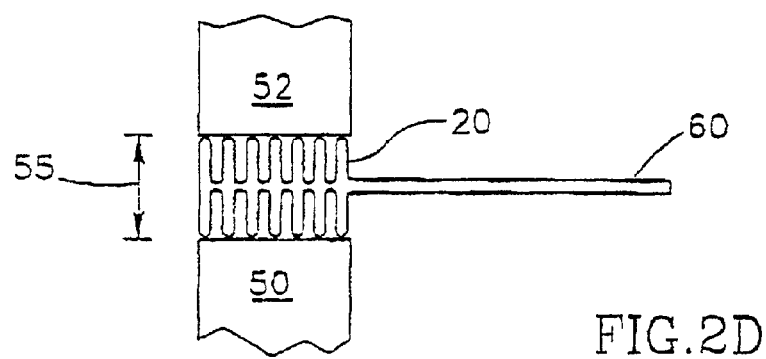

In FIG. 2D, spacer 20 is expanded over its entire length and it fills inter-vertebral space 55. In a preferred embodiment of the invention, a fixing material, such as a bone slurry or a setting fixing compound is provided into inter-vertebral space 55, in order to encourage fusion between vertebra 50 and vertebra 52. In the case of a bone slurry, bone chips or bone powder, such setting may require a week or so of bed rest. Preferably, spacer 20 is stiff enough to maintain its shape until the bone sets, so that little or no bed rest is required. Alternatively or additionally, at least some of the required stiffness is provided by the fixing material. Possibly, the fixing material degraded after a while and/or is a foam, to allow bone ingrowth. Alternatively or additionally, to injecting a fixing material or as part of the fixing material, growth hormones, enzymes, anti-bacterial pharmaceuticals, anti-inflammatory compounds and/or other bio-active materials may be injected into space 55, to encourage fusion and/or another desired effect.

Spacer Delivery Direction

In a preferred embodiment of the invention, the surgical approach is from the back of the patient. Alternatively, a lateral or a posto-lateral approach may be used. It is noted that the implanted spacer may be very narrow during implantation, so it is easier to plan and execute an approach, even through the abdomen. Alternatively or additionally, it is noted that the spacer, in some preferred embodiments of the invention, may be made flexible along its main axis, at least in its un-expanded configuration and especially as a result of the slits formed therein. Thus, the spacer can be provided at inter-vertebral space 55 using a curved guide, possibly a bendable guide, such as an endoscope. Alternatively, if the spacer is formed of a shape-memory material, the spacer may be cooled below the temperature at which it turns ductile, so that it can be easily bent. Alternatively or additionally, and especially if the spacer is elastic or super-elastic, the spacer may be maintained in a curved configuration during insertion using a curved stylet inserted through the spacer, alternatively or additionally to using a curved outer tube.

Guide Tube Insertion And Removal of Disc-Tissue Material

In a preferred embodiment of the invention, the spacer implantation process is performed through a guide tube, which connects intra-vertebral space 55 with the outside of the body. In general, provision of guide tubes to the spine is known in the art, for example for minimally invasive disk removal.

FIGS. 3A–3F illustrate a method of providing a sleeve 102, for use as a guide tube, into an intra-vertebral space, in accordance with a preferred embodiment of the invention.

FIG. 3A illustrates a guide wire 100 inserted into space 55. Such insertion is typically, but not necessarily performed using X-ray imaging guidance.

A combination sleeve-obturator is then inserted over guide wire 100, possibly requiring a small incision on the skin. A sleeve 102 preferably has a head 106 to which a head 112 of an obturator 110 can be fixed. A locking mechanism 114, for example using rotationally interlocking element, in which, for example, a half turn locks or unlocks the two heads, is preferably provided for locking the two head together. Obturator 110 also includes an inclined tip 108, preferably situated at its proximal end to aid in forcing the device through the tissue. A body stopper 104 is preferably provided, which can be positioned along the axis of sleeve 102, to prevent the sleeve from advancing too far into the body. Typically, an initial estimate for the body stop position can be determined from the X-ray images and a more exact position can be determined once the sleeve is inserted, for example from fluoroscopic images. Preferably, but not necessarily, the sleeve diameter is large enough such that the sleeve itself cannot enter all the way into space 55. Preferably, different sleeve sizes are used for different parts of the spine. Optionally, the sleeve size and/or geometry (e.g., barbs) is such that once the sleeve is inserted it is fixed in place and cannot be inadvertently retracted, except by application of significant force. Alternatively, The sleeve tip may include an extending barb or an expanding ring, to hold it in place.

Figure 3C:
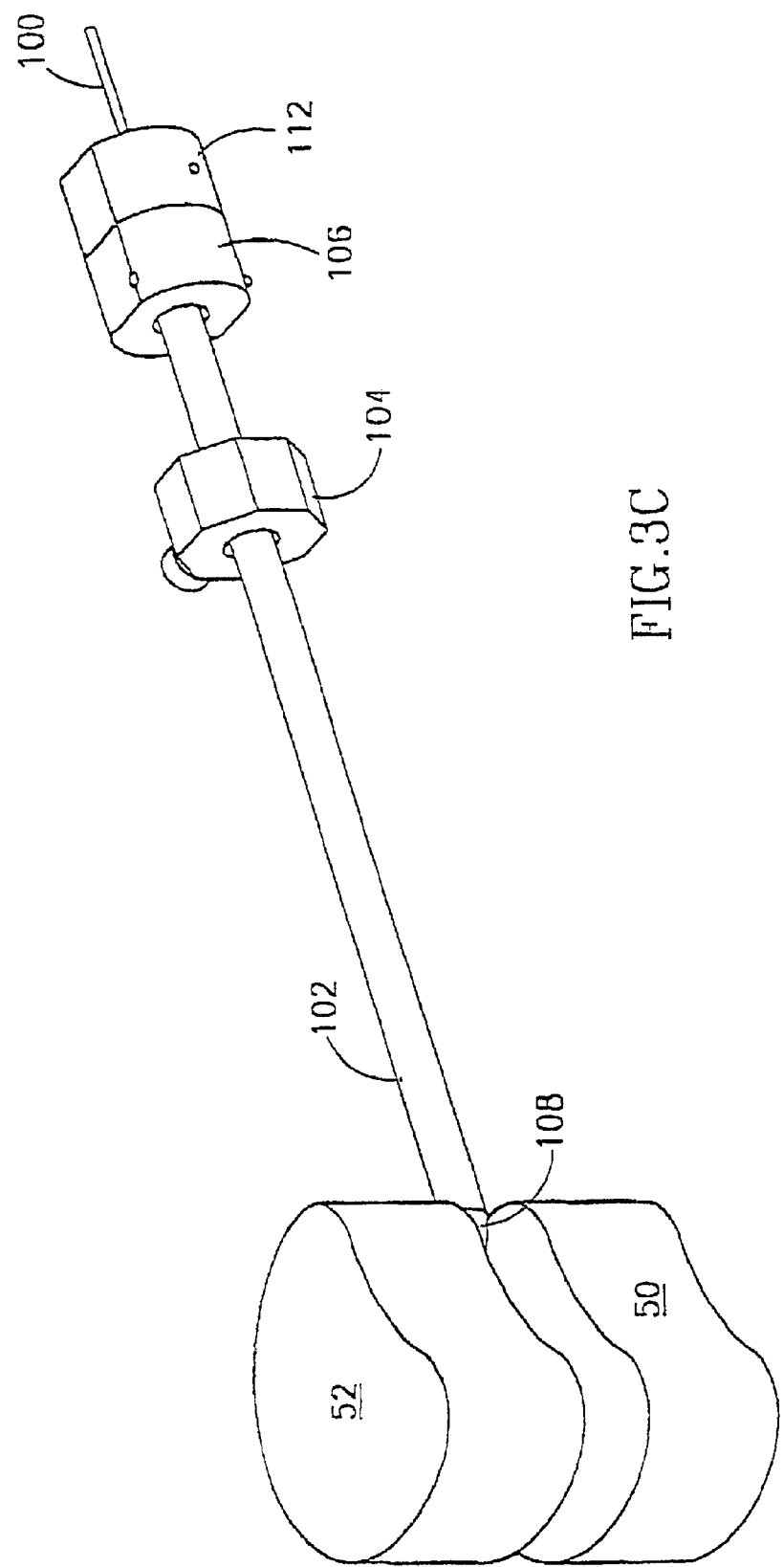

FIG. 3C is a perspective view of FIG. 3B.

In FIG. 3D, obturator 110 is retracted, leaving sleeve 102 in place.

In FIG. 3E a trephine 116 is provided through sleeve 102, to perforate an annulus fibrosus capsule of space 55, using a cutting tip 118 of the trephine. Preferably, a head 120 of trephine 116 includes a slipping mechanism 122, so that it can freely rotate on head 106, and not lock as obturator 110 does.

Figure 3F:
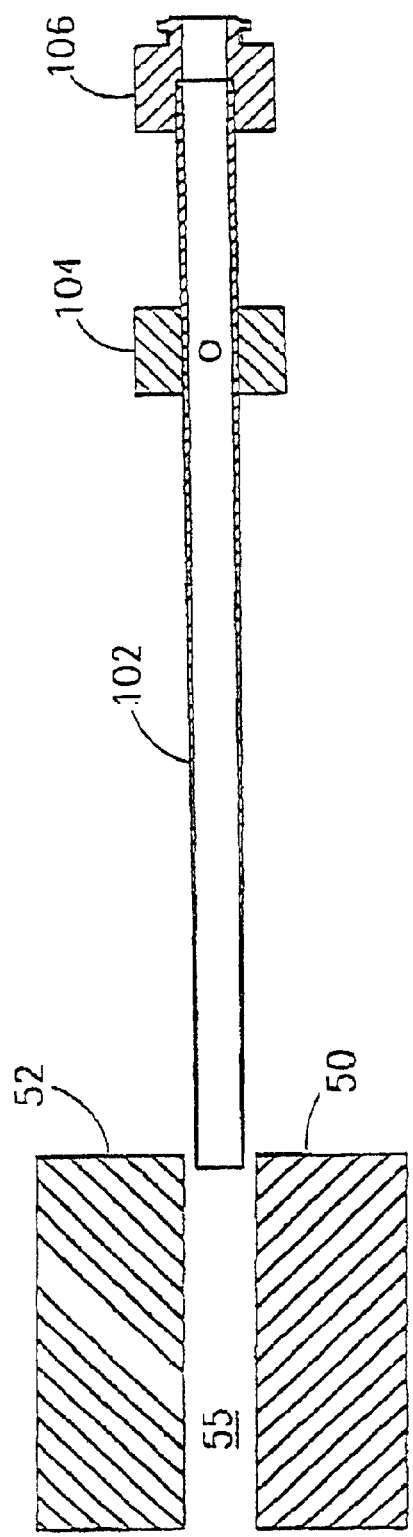

In FIG. 3F, both trephine 116 and guide wire 100 are retracted, leaving sleeve 102 in place.

At this point the disc material is preferably removed. Optionally, the end-plates of the vertebrae are also removed.

Optionally, a plurality of holes are formed in the end-plates and/or the vertebrae, which holes may promote bone growth. Such holes may be formed using many tools, for example, a bent guide wire, a bent-tip trephine, a rotoblator or a punching device. Preferably, a bendabletip endoscope is used, to guide the hole cutting tool to a desired location.

Exemplary Guide Set

FIGS. 4A–4F illustrate an exemplary set of tools for performing the method of FIGS. 3A–3F.

Figures 4A, 4B:
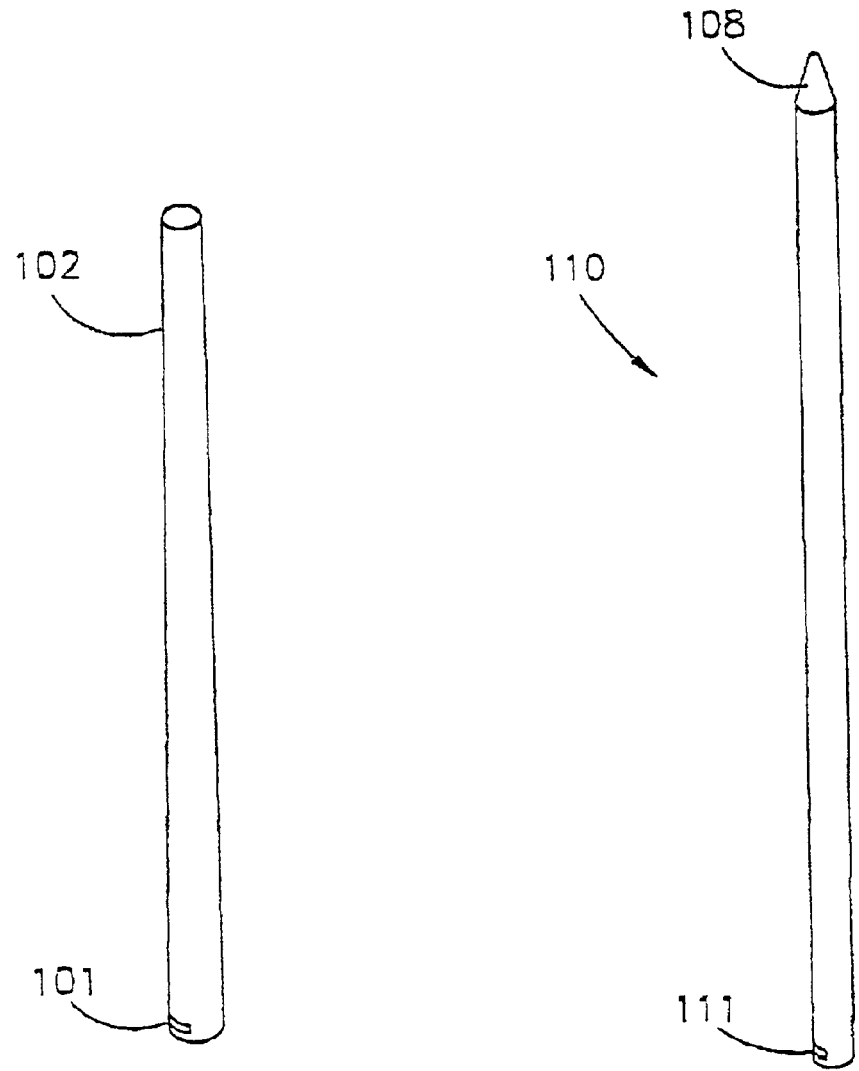
FIGS. 4A–4F illustrate an exemplary set of tools for performing the method of FIGS. 3A–3F, in accordance with a preferred embodiment of the invention.

FIG. 4A illustrates an exemplary sleeve 102, having a slot 101 formed near one end, for attaching head 106 to the sleeve. In the exemplary embodiment shown, the inner diameter is 6 mm; the outer diameter at the head end is 8 mm and the outer diameter at the tip end is 6.5 mm. An exemplary length is 149 mm sleeve length, between the head and the tip.

FIG. 4B illustrates an exemplary obturator 110, having a slot 111 formed near one end, for attaching head 112 thereto. In the exemplary embodiment shown, a bore of 1.3 mm is formed for guide wire 100, from tip 108 to the head end of obturator 110. Optionally, about 30 mm from tip 108, the bore widens to a 3.0 mm diameter. Tip 108 is 7.84 mm long, with a minimum tip diameter of 1.8 mm. The length of obturator 110 is preferably 180 mm long, including a part that is inside head 112. The outer diameter of obturator 110 is preferably 6mm or slightly less.

Figure 4C:
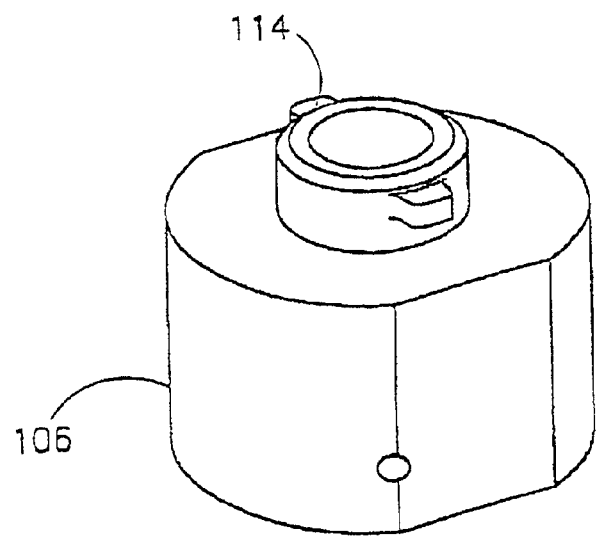

FIG. 4C is a perspective view of an exemplary head 106 for sleeve 102, showing a part of locking mechanism 114 that is formed in head 106. A bore of 1.3 mm is preferably formed in the head for guide wire 100.

Figure 4D:
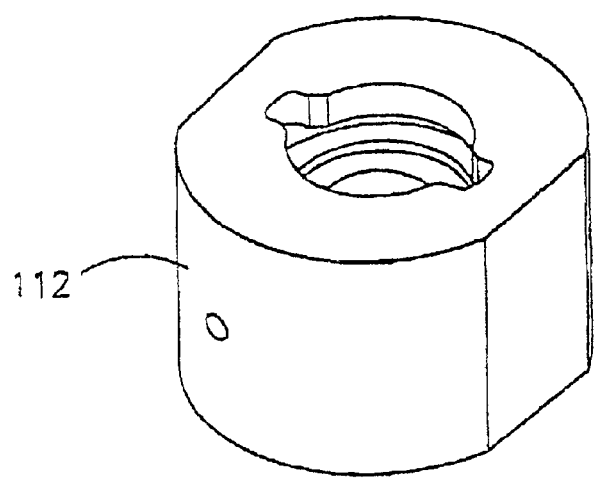

FIG. 4D is a perspective view of an exemplary head 112 for obturator 110, showing. the rest of locking mechanism 114. A bore of 1.3 mm is preferably formed in the head for guide wire 100.

Figure 4E:
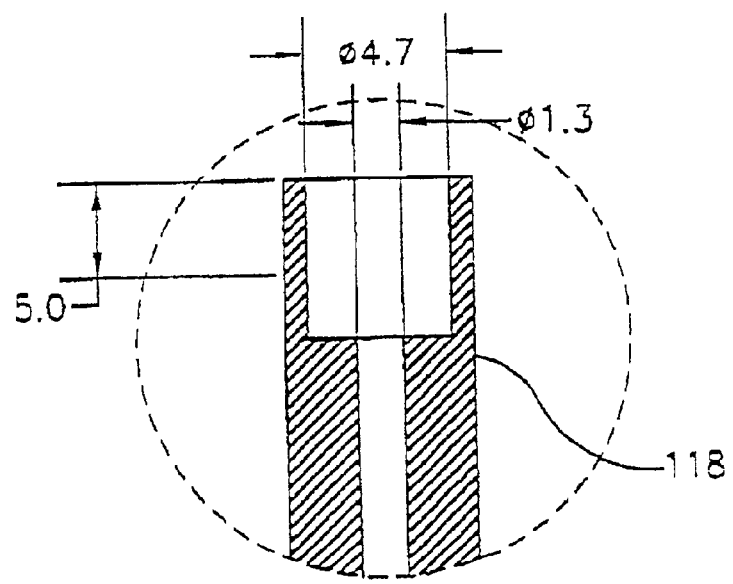

FIG. 4E illustrates a detail of a tip 118 of an exemplary trephine 116, in accordance with a preferred embodiment of the invention. In general, form, such as length, diameter, slot and bore, trephine 116 can be the same as obturator 110. Tip 118 includes a 5 mm section that has an inner diameter of 4.7 mm and is preferably serrated or sharpened (not shown) at its distal end, so that it can be easily rotated.

Figure 4F:
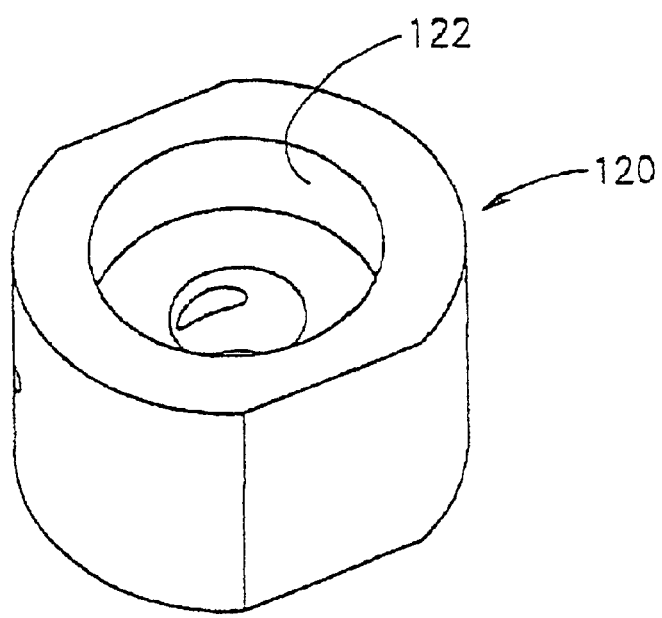

FIG. 4F illustrates a head 120 for trephine 116, also illustrating a hollow inside portion for completing free-turning mechanism 122. A bore of 1.3 mm is preferably formed in the head for guide wire 100.

Space Measurement Apparatus

Figure 5A:
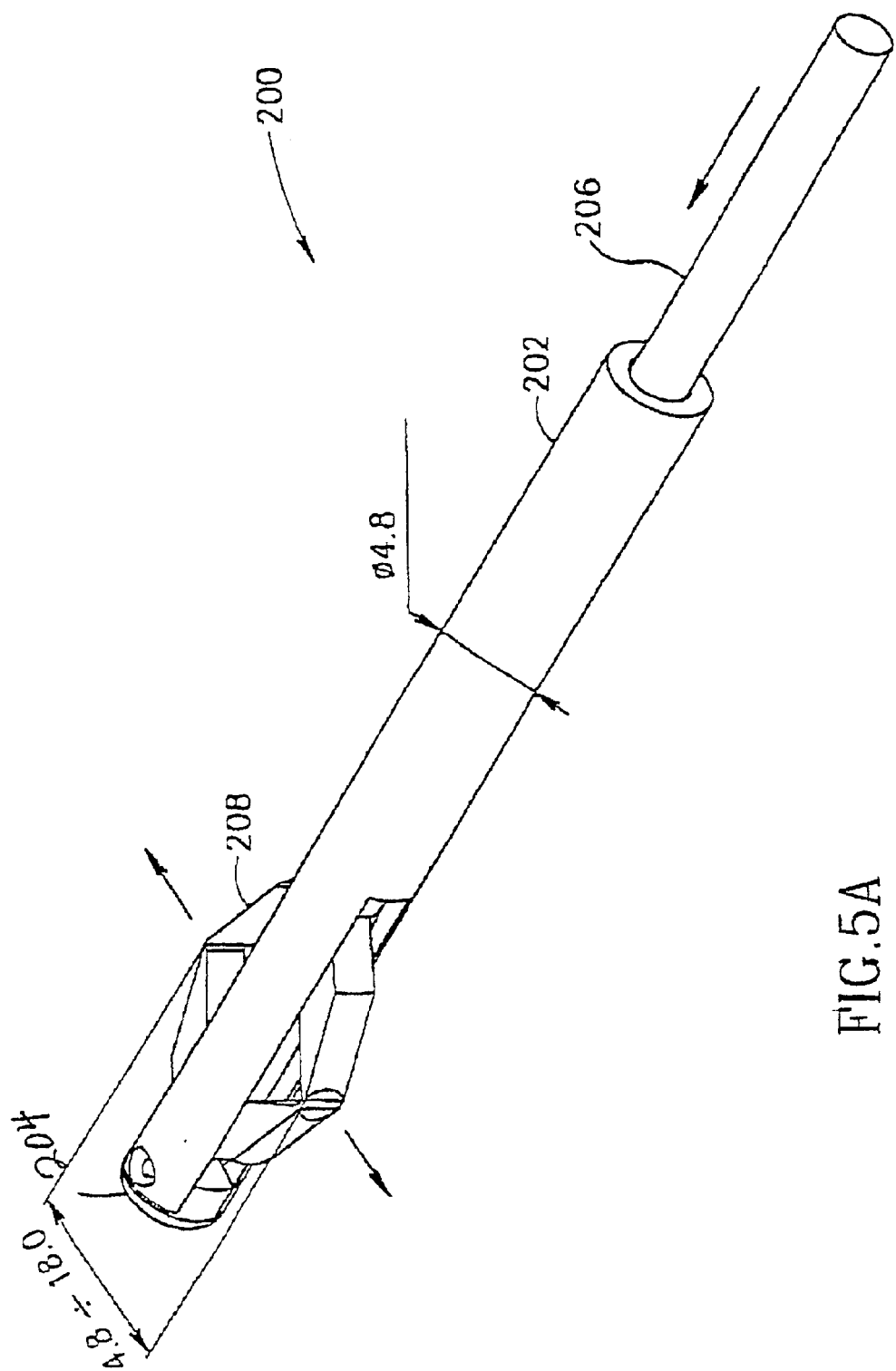
FIGS. 5A–5C illustrate an intra-vertebral measurement device, in accordance with a preferred embodiment of the invention.
Figure 5B:
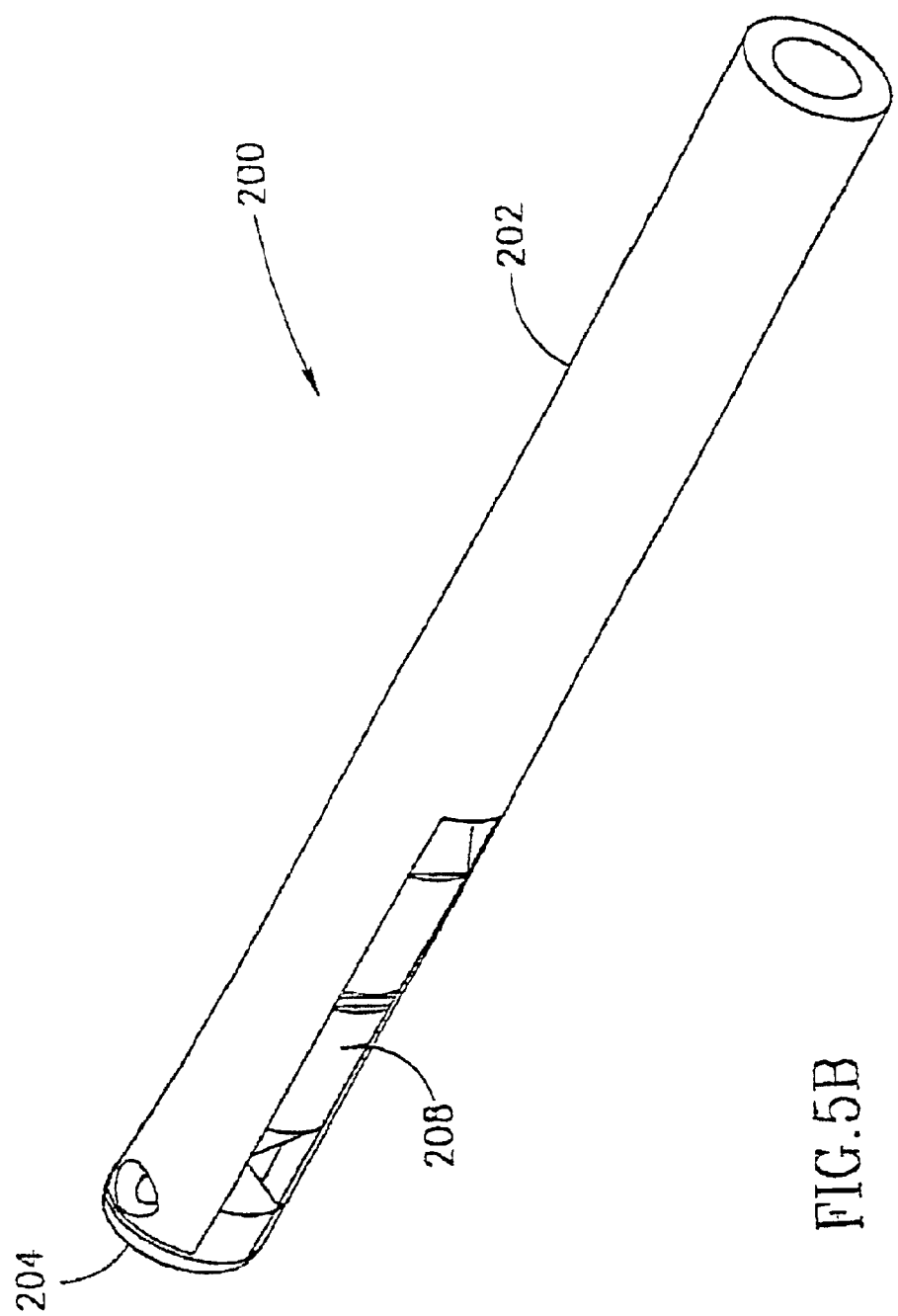
Figure 5C:
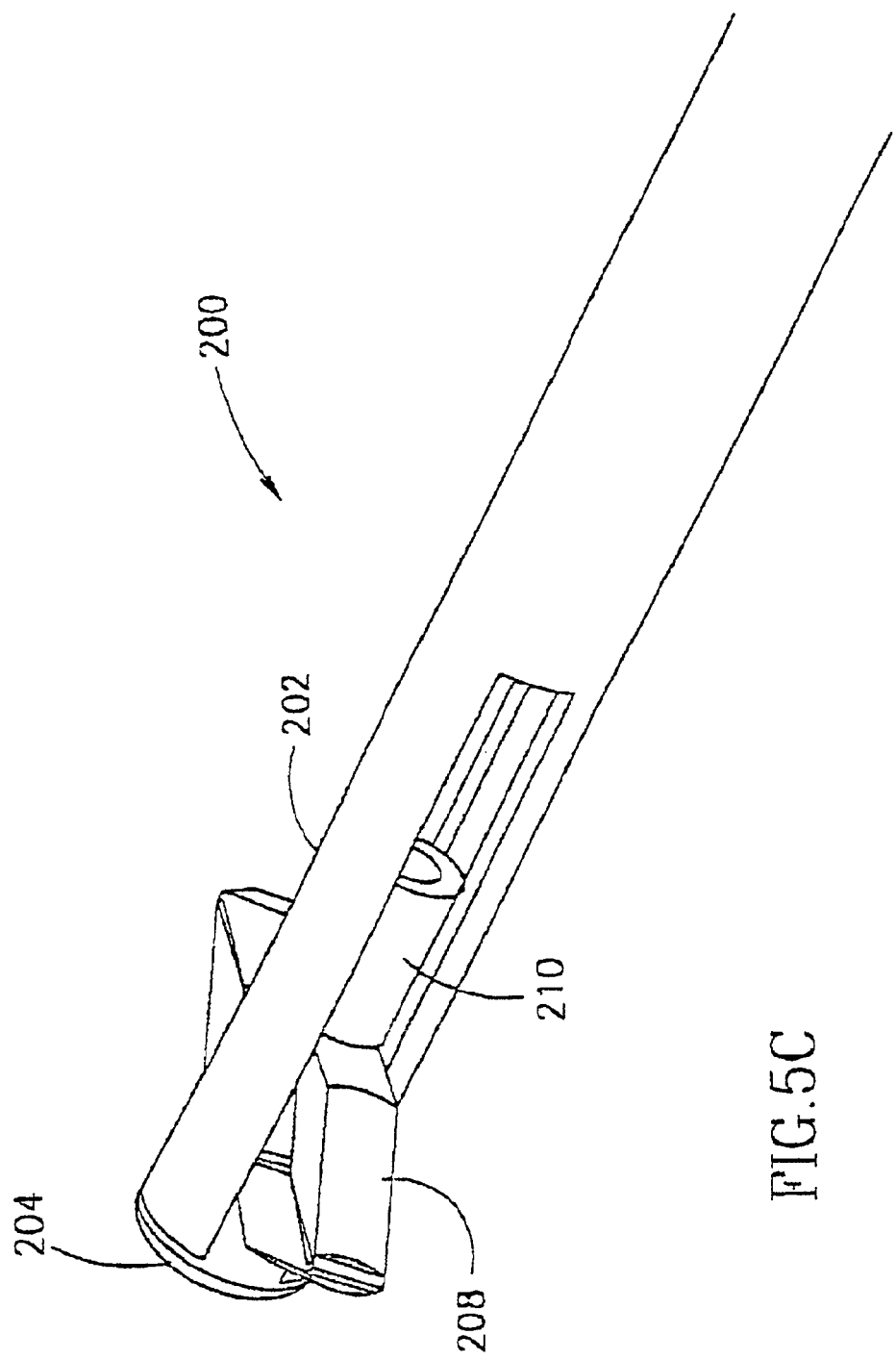

FIGS. 5A–5C illustrate an exemplary intra-vertebral measurement device 200, in accordance with a preferred embodiment of the invention. Device 200 is preferably used to measure the distance between vertebrae 50 and 52 and/or other dimensions of space 55, to better select a spacer to fit and/or for exerting control over the spacer expansion, so that it matches the physical geometry of the patient.

In some cases, it is sufficient to make one measurement in space 55. In others, the measurement is repeated in several locations in space 55.

As shown in FIG. 5A, exemplary device 200 comprises a slotted tube 202 having a cap 204 and a bore. A shaft 206 is inserted into the bore of tube 202. A plurality of wings 208 are preferably connected on one end to shaft 206 and abut cap 204 at their other end, so that when shaft 206 is advanced, wings 208 extend. When wings 208 meet physical opposition (such as bone), they stop extending, so the advance of shaft 206 is stopped. The amount of movement of shaft 206 can be used as an indication of the measured dimension. Shaft 206 and tube 202 are preferably, but not necessarily flexible, so that they can be centered by wings 208 in space 55.

Length of space 55 can be measured by detecting the extreme locations along the width of the space where wings 208 do not extend freely, as being the edges of space 55.

Width and height of space 55 can be determined by rotating device 200 to an orientation at which they extend axially to the spine and taking a measurement. These measurements may be repeated at several points along space 55, by axially retracting and advancing tube 202. In some embodiments, tube 202 is bent or bendable, so that non-axial measurements can be taken.

In the exemplary embodiment shown, the outer diameter of tube 202 is 4.8 mm and wings 208 can extend to a maximum diameter of 18 mm. However, in other implementations, other sizes may be provided. For example, if device 200 is used for measurement of intramedullar channels, a smaller diameter device may be provided, for example having a diameter of 3 or 2 mm. A larger range of radii may also be required, for example, between 2 and 40 mm. Alternatively, a smaller range of radii may be provided, for example between 4 and 8 mm.

FIG. 5B shows device 200 (with shaft 206 hidden) with wings 208 closed.

FIG. 5C shows device 200 (with shaft 206 hidden) with wings open. Wings 208 are preferably attached to a head 210, which head may molded onto shaft 206. Shaft 206 is preferably metal, while head 210 and wings 208 are preferably a single piece of plastic. Alternatively, shaft 206 may be plastic, possibly a single unit with wings 208.

In the exemplary embodiment shown, wings 208 form a parallelogram or a diamond, such that compressing an axial (of the shaft) axis of the parallelogram increases the other (transaxial of the shaft) axis, thereby extending wings 208. When the shaft is retracted, for example using a spring, the transaxial axis is decreased, so the wings retract. In some embodiments, the spring-back of wings 208 themselves is used for retracting the wings. In an alternative embodiment, the shaft comprises at its end a cone, which, when retracted, pushes the wings out of the slots. Many other alternate mechanisms may be used.

Trigger and Display Mechanism

Figure 6:
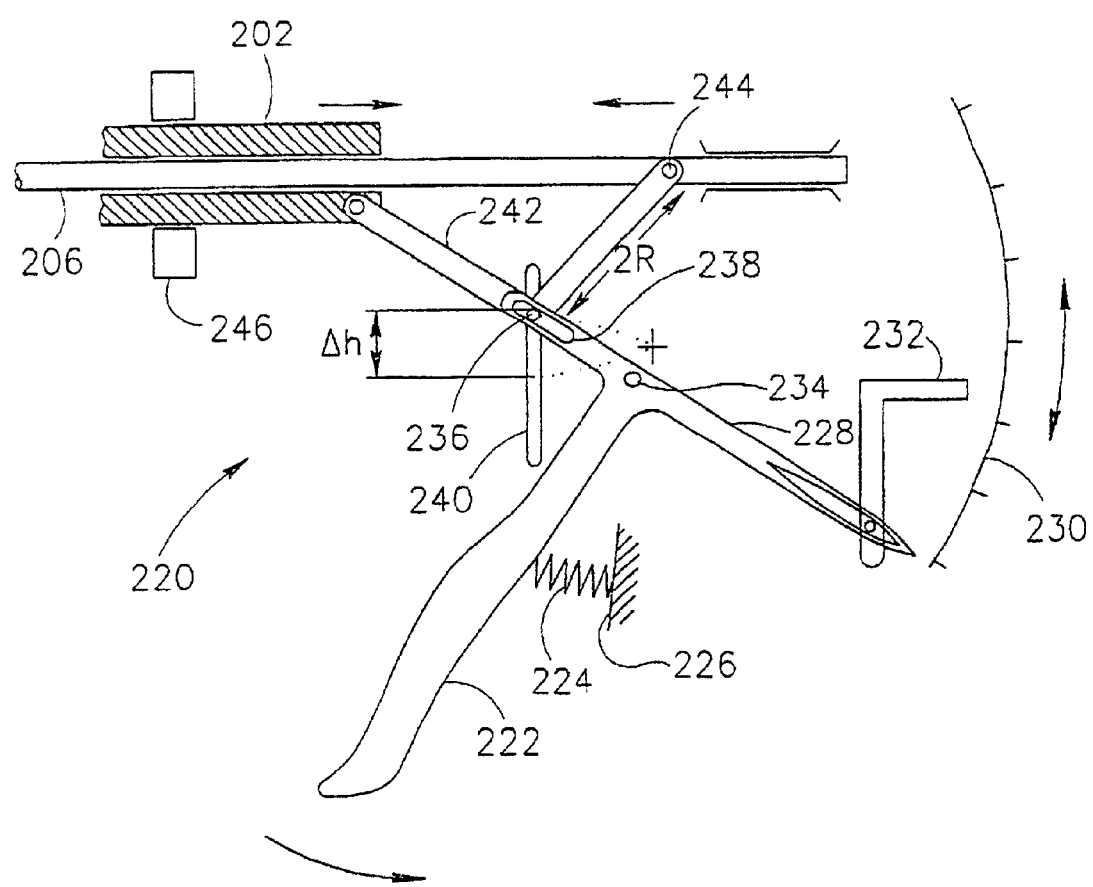
FIG. 6 illustrates a trigger and display mechanism for the measurement device of FIGS. 5A–5C, in accordance with a preferred embodiment of the invention.

FIG. 6 illustrates a trigger and display mechanism 220 for the measurement device of FIGS. 5A–5C. Mechanism 220 comprises a trigger 222 attached to an axis 234. One end 228 of trigger 222 can serve as a dial indicator 228 for indicating a position on dial 230. An optional dial extension 232 may be provided. A spring 224 coupled to a base 226 and trigger 222 is preferably provided to return trigger 222 to a resting position and to retract shaft 206.

A bent arm 242 interconnects tube 202, shaft 202 (at point 244) and trigger 222, (using a pin 236). Pin 236 is free to slide in a slot 240 in the body (not shown) of the measurement system) and a slot 238 of trigger 222. This mechanism provides both spring back of the shaft and converts the motion of the shaft into a scale that linearly shows the wing extension.

Other conversion mechanisms, such as using non-linear gears and eccentrically moving gears, may be used instead.

An axial stopper 246 is preferably provided to control the axial position of the measurement system relative to the patient, allowing measurements in different parts of space 55. Other mechanisms, such as a screw-connection to sleeve 102 may also be used.

In a preferred embodiment of the invention, system 200 is held with one hand, freeing the other hand to do other operations.

General Spacer Expansion Control

Figure 7A:
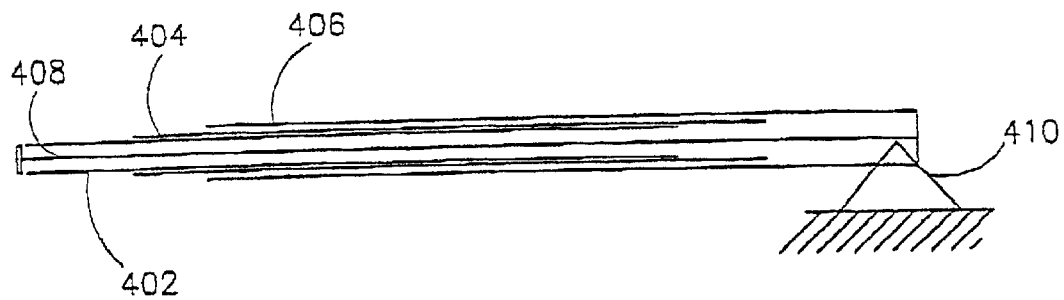
FIGS. 7A–7F illustrate, schematically, a method of deploying the spacer of FIGS. 1A–1D, in accordance with a preferred embodiment of the invention.
Figure 7B:
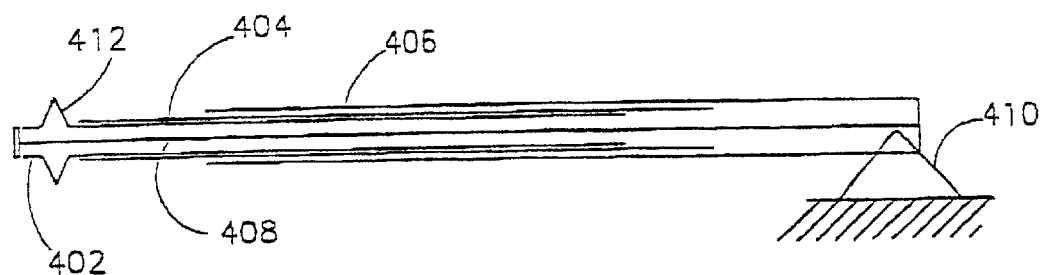
Figure 7C:
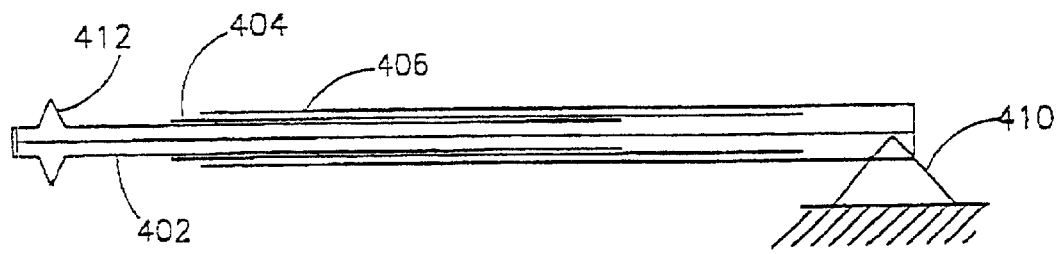

FIGS. 7A–7C illustrate an exemplary method of spacer expansion, in accordance with a preferred embodiment of the invention. A spacer 402 is provided as a tube having an inner bolt 408, which bolt is preferably configured to prevent the advance of the end of spacer 402, past the end of the bolt. An outer collar 404 is provided for shaping the expansion of the spacer. A laproscopy tube 406 is also shown. In this embodiment, both bolt 408 and tube 406 are fixed to a base 410 outside the body. This base may be, for example, fixed to the patient and/or his bed or it may be prevented from advancing towards the body by other means. Thus, the base of the spacer does not advance into the body. In other embodiments described below, the bolt may be retracted, requiring the base 410 to advance or to move relative to bolt 408, if the spacer is to maintain its place in the body during expansion.

FIG. 7A shows a starting position, with bolt 408 and spacer 402 (in its unexpanded state) extending between two vertebrae (not shown).

Both spacer 402 and collar 404 are advanced. However, as the spacer is prevented from advancing by bolt 408, it expands, at the areas where expansion is not prevented by collar 404, forming one or more spikes 412. This result is shown in FIG. 7B.

Collar 404 is then retracted (FIG. 7C), so that both the collar and the spacer can be advanced again.

Figure 7D:
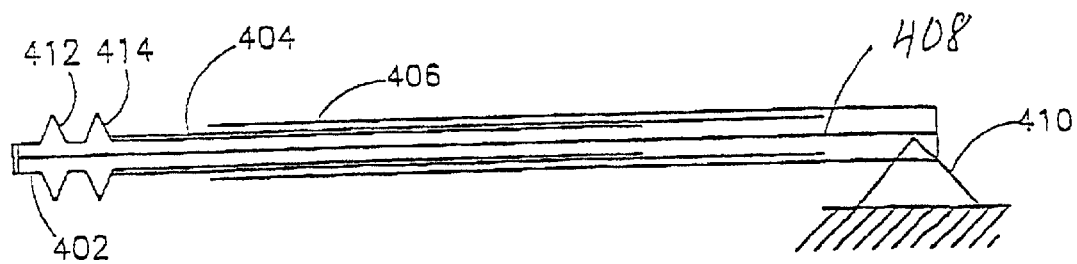

In some embodiments, the spike size is different for different spikes, requiring a different amount of motion for expanding each spike. Different amounts of motions can be required for other reasons as well, for example to allow better control over the spike expansion. In some cases, the spacer exhibits a spring-back effect, in that the spikes, after being extended, spring back and axially extend the spacer. The amounts of motion preferably take the spring-back, as well as the plastic deformation, into account. In FIG. 7D, collar 404 and spacer 402 are advanced by a different amount than in FIG. 7A, to create a second spike 414.

Figure 7E:
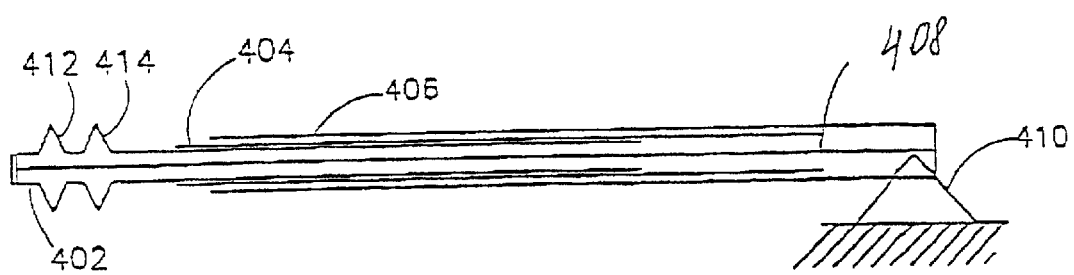
Figure 7F:
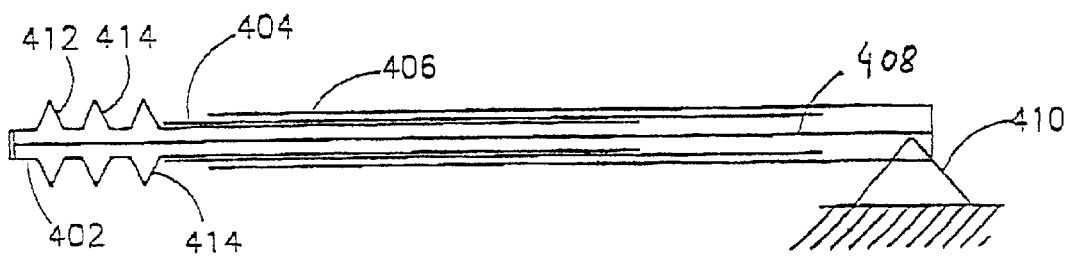

In FIG. 7E, collar 404 is retracted by a different amount from FIG. 7B, allowing a third spike 416 to expand out (FIG. 7F).

Deployment System

FIGS. 8A–11 show several devices suitable for expanding a spacer in ways similar to that shown in FIGS. 7A–7F. These devices may also be used for controlled deployment of other implants in the body, where the relative positions and/or orientations of several elements are modified to effect or allow a certain deformation of an implant.

In the following devices, linear motion of the spacer, bolt and/or collar is provided. However, in some embodiments, rotational motion, alternatively or additionally to linear motion, may be acceptable or desirable. For example, spiral motion of collar 404 is generally acceptable. Rotational motion of spacer 402 is generally not acceptable, however, a slip-ring may be provided between a pusher tube that exhibits a spiral motion and a spacer that does not. In some embodiments, collar 404 is not rotationally symmetric, for example including slits for expansion of spikes therethrough, in which case rotational control of the collar angle may be advantageous.

Also, although discrete motion of the elements is generally preferred, in some embodiments, simultaneous, continuous motion of elements (such as a bolt and a collar), even during spike expansion, are provided.

In the embodiments below, collar 404 is outside of spacer 402. However, collar 404 can be inside spacer 402, if it engages the inside of the spacer and prevent expansion at the engaged areas, for example using a threading.

Manual Deployment Device Embodiment

FIGS. 8A–8D illustrate a delivery control system 500 for effecting the process shown in FIGS. 7A–7F, in accordance with a preferred embodiment of the invention.

In general, system 500 includes two sub-systems, a collar retraction subsystem and a spacer advancement sub-system. Bolt 408 is fixed to a handle 502 of system 500.

Each of the subsystems includes a knob for effecting the motion, means for converting rotational motion of the knob into linear motion of the moved element and a lock for stopping the motion once the required extent of motion, for a particular spike expansion, has be performed. In a preferred embodiment of the invention, the lock comprises a plate having a plurality of holes formed in it and a pin, which slides along the plate and is elastically urged into a hole. The distance between the holes corresponds to the amount of motion desired in each expansion step.

In operation, a user advances collar 404 and spacer 402 using the spacer advancing subsystem, until a pin fits in a spacer location plate (corresponding to FIGS. 7A–7B). Then, the user retracts collar 404 using the collar retraction subsystem, until a pin fits in a collar location plate (corresponding to FIGS. 7B–7C). The user then frees the pin from the spacer location plate and advances the spacer and collar again (corresponding to FIGS. 7C–7D). Then the user frees the pin from the collar location plate and retracts the collar (corresponding to FIGS. 7D–7E). This process is repeated until the spacer is properly deployed. A pole element that holds bolt 408 is released from the bolt and system 500 is retracted. In an exemplary embodiment, the pole is threaded on the bolt, so system 500 is rotated around its axis to free the bolt. Preferably, a screw fixing system 500 to its handle 502 is released, allowing easier rotation of system 500 and/or of the pole element. In some embodiments, the spacer is locked to the bolt by advancing the pole-element by screwing it in tighter.

In a preferred embodiment of the invention, at the end of the spacer expansion, an optional additional spacer advancing step is performed, to compensate for the spring-back of the spacer and allow the cap-locking mechanism of the spacer to be deployed.

Although a particular implementation of the above described device is shown, other implementations may be provided instead, while maintaining the general scheme of operation described above.

Figure 8A:
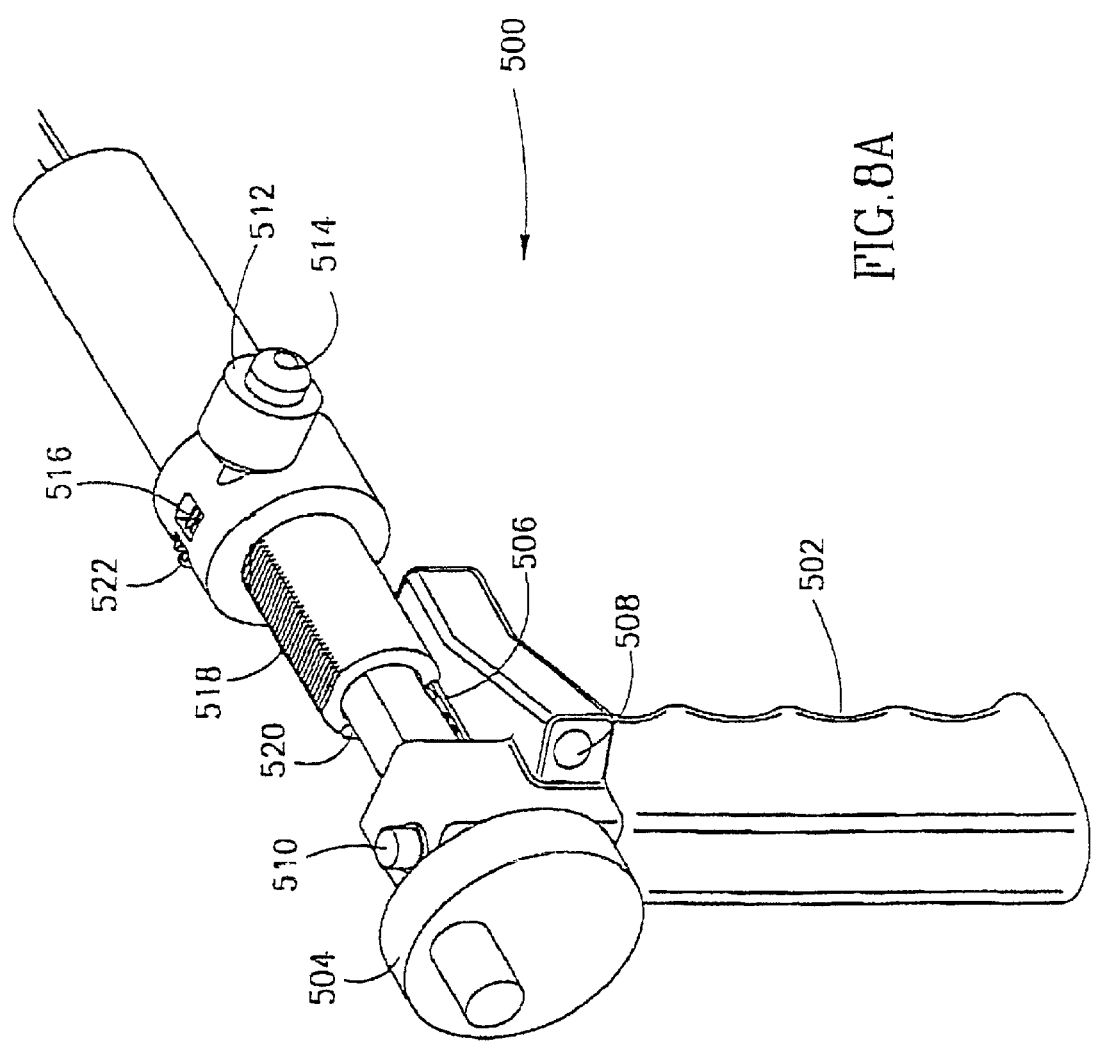
FIGS. 8A–8D illustrate. a delivery control system for affecting the process shown in FIGS. 7A–7F, in accordance with a preferred embodiment of the invention.

FIG. 8A is a side perspective view of device 500, showing a knob 504 that is part of the spacer advancement subsystem. Spacer location plate 506 can be seen in side profile. A button 508 for freeing the pin (not shown in this figure) from spacer location plate 506. A button 510 frees the rest of system 500 to rotate relative to handle 502. As the spacer advancement generally requires great force, knob 504 preferably includes a significant lever and/or gear-reduction. Preferably, button 510 is used after the spacer is locked to its bolt and/or the pole-element has been at least partly unscrewed, however, this is not essential.

A knob 512 is provided as part of the collar retraction subsystem. A gear 516, rotated by knob 514, engages a linear gear 518. A collar location plate 520 can be seen on edge. A pin locking mechanism 522, will be described below. A button 514 on knob 512 is used to release mechanism 522 and the pin from collar location plate 520.

Figure 8B:
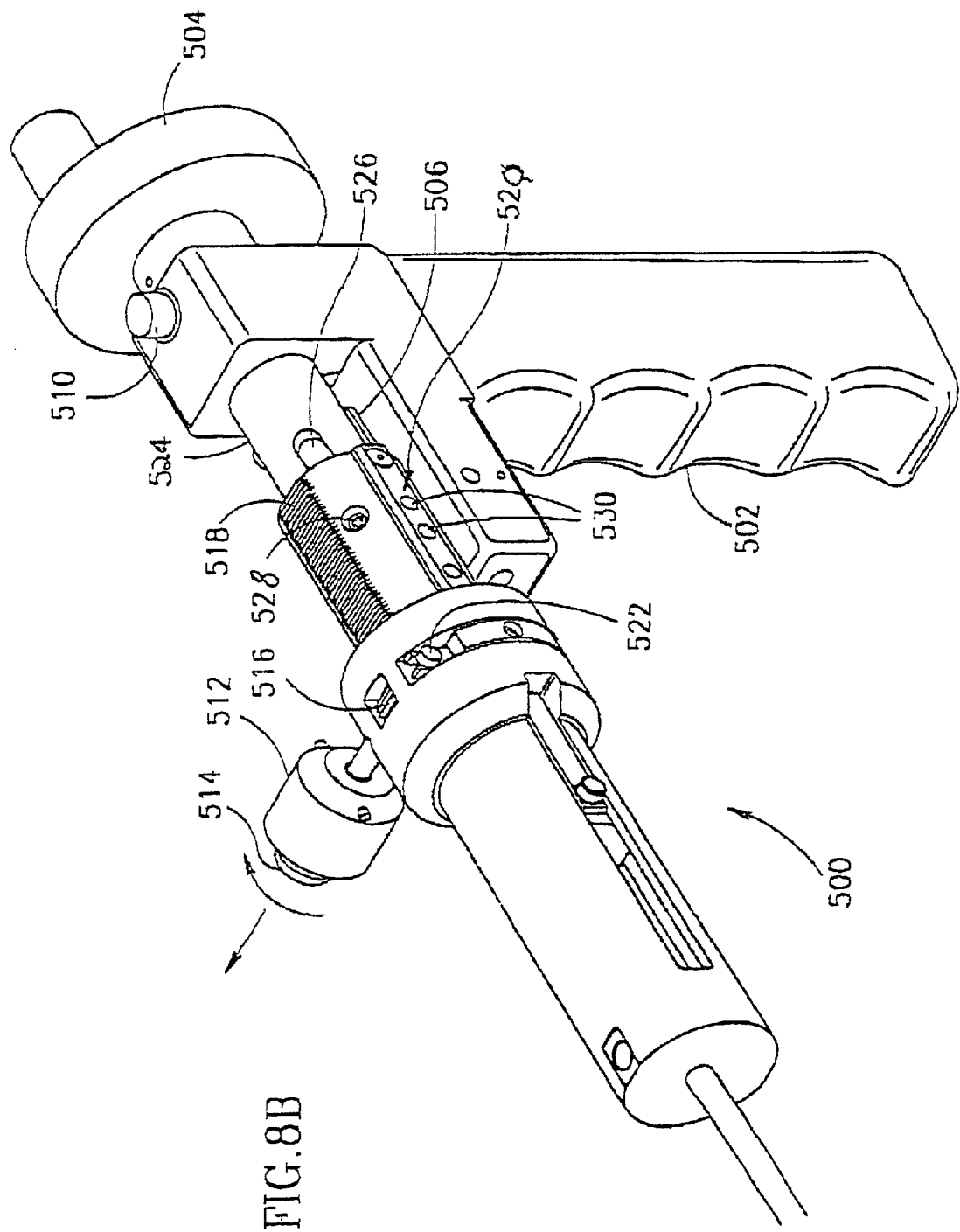

FIG. 8B is a perspective view of system 500 from its other side, showing locking mechanism 522 and collar location plate 520 in greater detail. In particular, a plurality of holes 530 in collar location plate 520 are shown.

Spacer advancement is achieved by the rotation of knob 504 advancing a free-turning (or counter-threaded) bolt (not shown in this figure) having a plurality of pins 528 extending trans-axially from it. These pins are engaged by slots 526 in a tube 524, restricting the bolt (and the spacer advancing system) to linear motion.

Figure 8C:
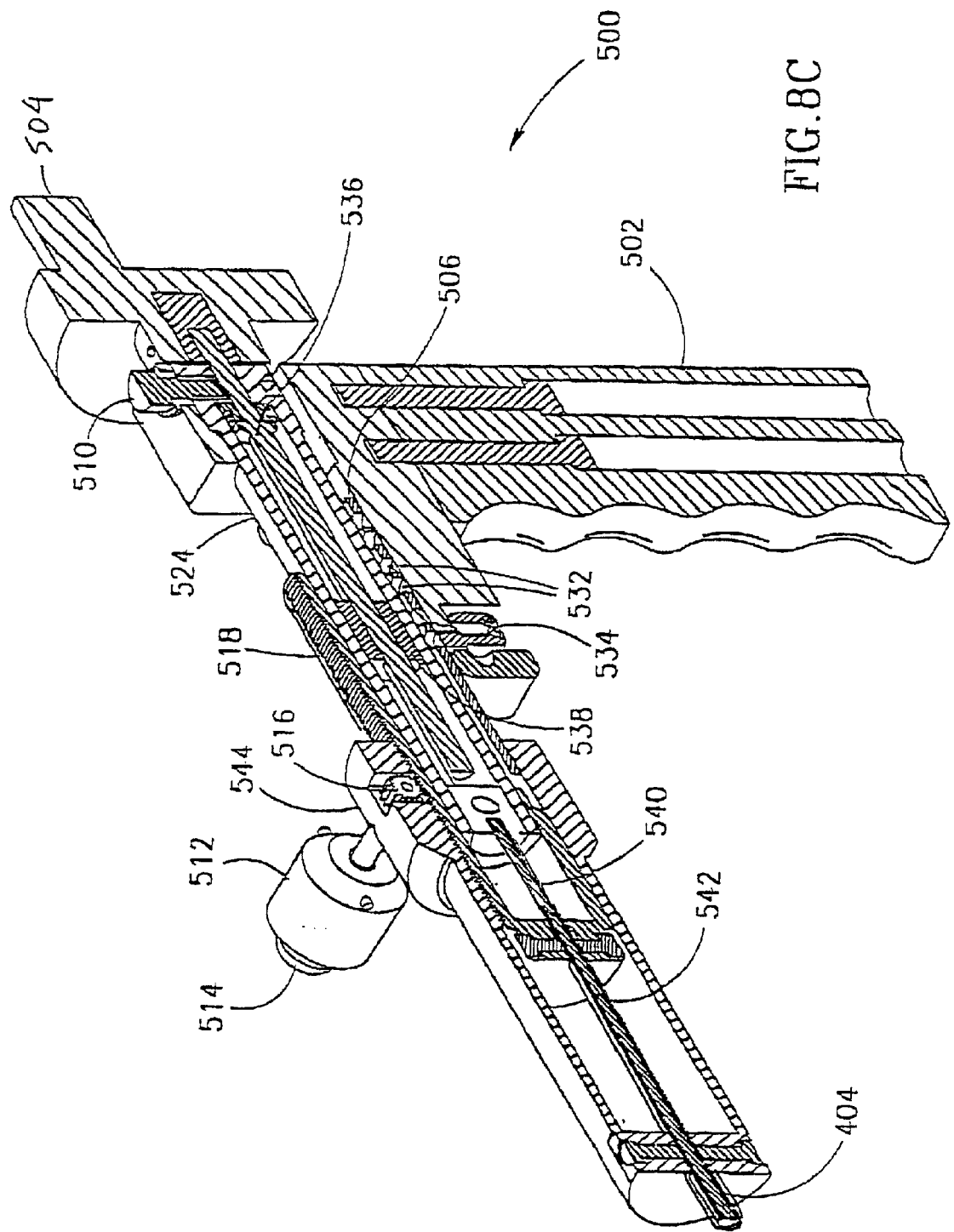

FIG. 8C is a cut-through view of FIG. 8B, showing spacer location plate 506 in greater detail, especially a plurality of holes 532 for an elastically biased pin 534 to engage, when the pin is adjacent one of the holes.

Knob 504 turns a threaded axis 536, having mounted on it a free-rotating, threaded or a counter threaded bolt 538 (from which pin 528 extends).

A pole element 540, that engages bolt 408 (not shown) is fixed in place relative to handle 502. A spacer pushing rod 542 is only affected by the motion of linear gear 518. A collar 404 is advanced by the motion of linear gear 518 and retracted by the motion of a collar retraction assembly 544 coupled to gear 516.

A solution for unthreading pole element 540 from bolt 408, alternative to using button 510 (FIG. 8A) is to extend pole element 540 through threaded axis 536, until knob 504. A button (not shown) may be provided to couple the rotation of knob 504 to element 540 or a separate knob may be provided. Thus, when deployment of the spacer is completed, pole element 540 can be easily rotated. This solution may also be applied to the other embodiments described below.

Figure 8D:
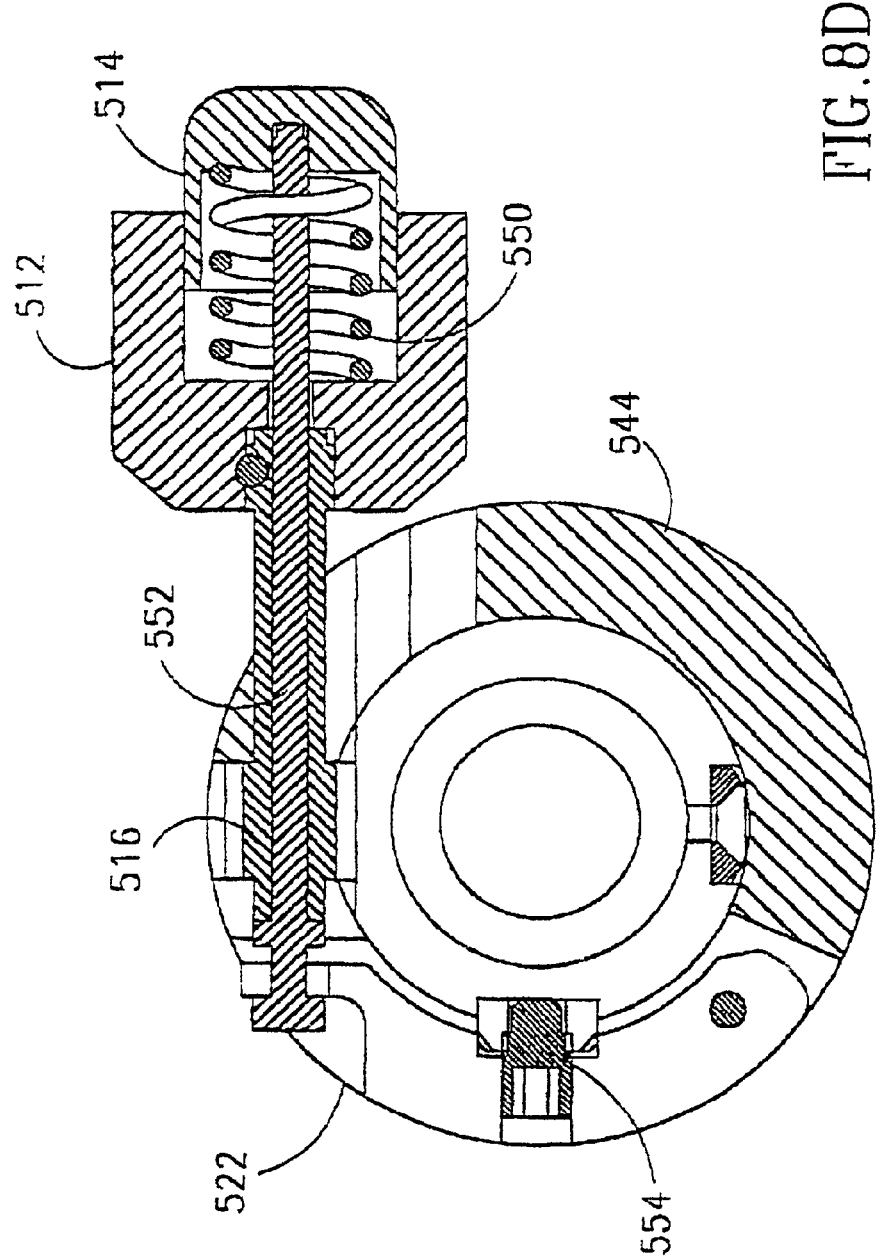

FIG. 8D illustrates the locking mechanism for the collar motion in greater detail. A pin 554 is urged by a spring 550 in knob 512 to engage collar location plate 520 (not shown). A rod 552 couples release button 514 and locking mechanism 522, to retract pin 554 from the collar location plate, when needed.

Alternating Pin Embodiment

Figure 9B:
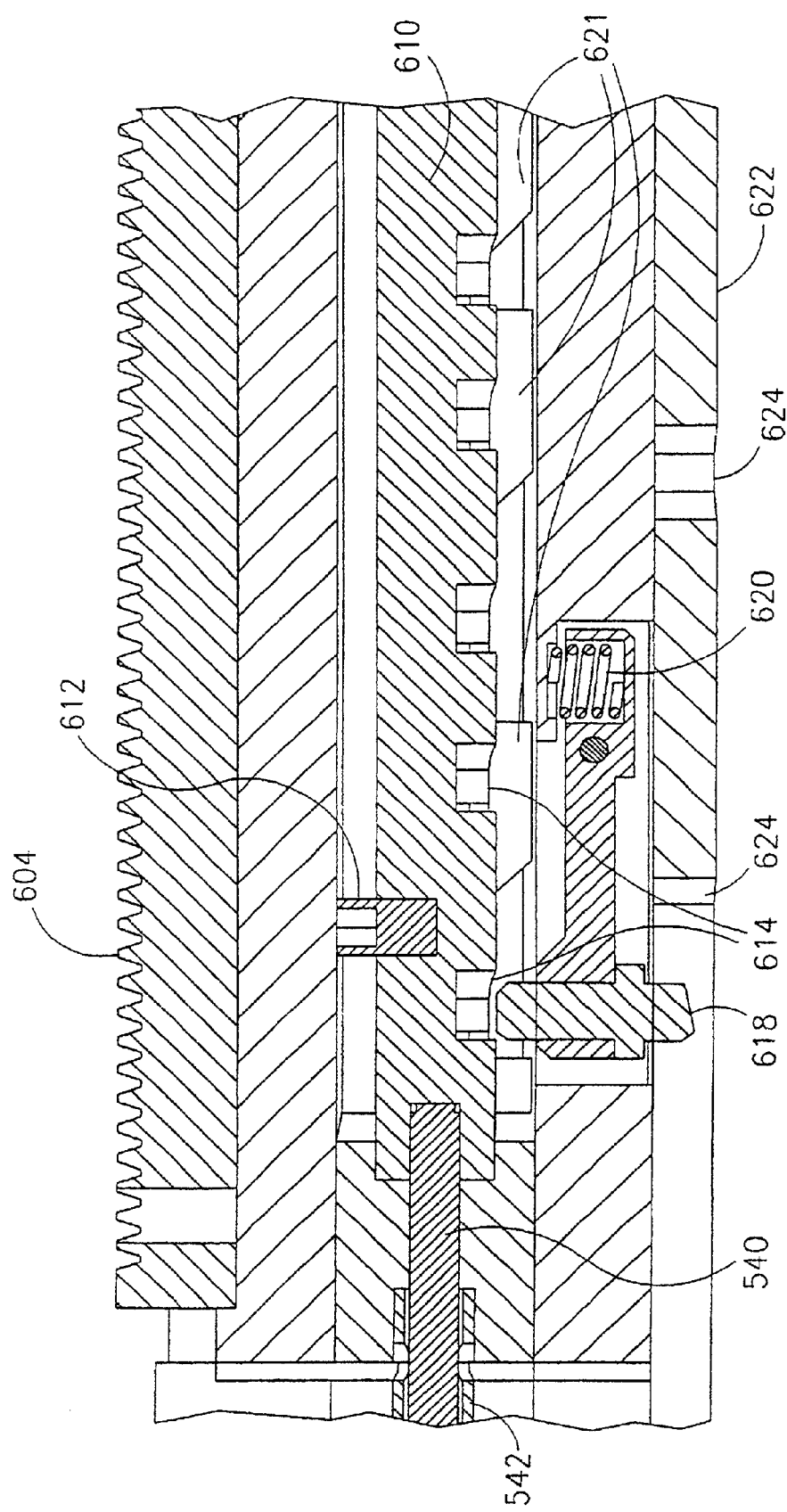
Figure 101:
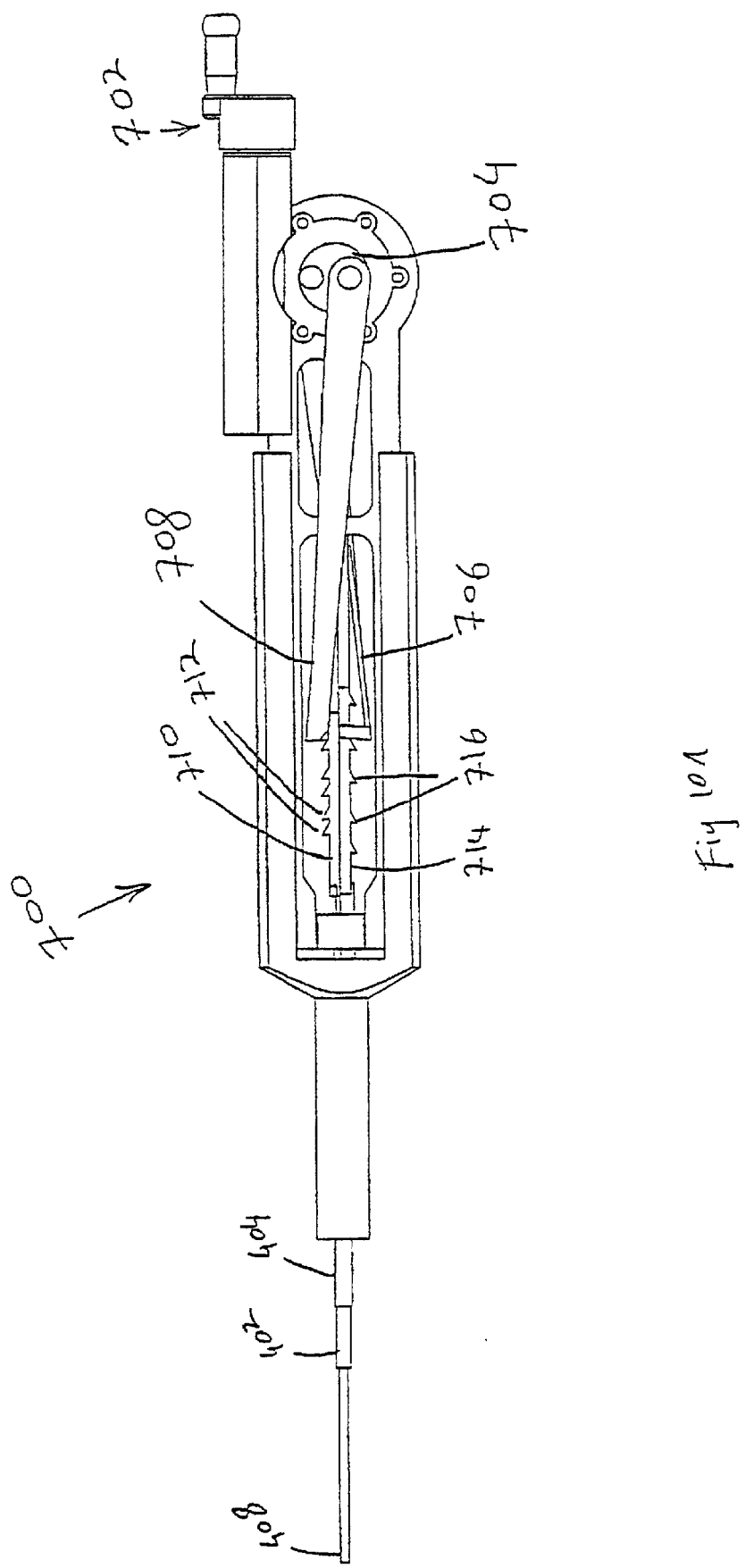

FIGS. 9A–9B illustrate a delivery control system 600, utilizing an alternating pin, in accordance with a preferred embodiment of the invention.

Unlike system 500 of FIGS. 8A–8D, system 600 uses a continuous rotational motion of a gear 606 to retract a linear gear 604 and components attached to it (described below) through an opening 608 in a handle 602 of system 600.

Another difference from system 500 is that in system 600, as implemented, spacer 402 is not advanced, instead, both bolt 408 and collar 404 are retracted.

FIG. 9B shows in detail an alternating pin mechanism for selectively retracting with linear gear 604 either collar.404 or bolt 408.

Pole element 540, which retracts bolt 408 is fixed to a bolt-retractor 610. A pin 612 is provided to prevent rotation of retractor 610 and/or prevent un-powered axial motion of retractor 610.

A plurality of holes 614 are formed in retractor 610 for receiving a pin 618. When pin 618 is in one of holes 614, linear gear 604 is coupled to retractor 610, by pin 618, so that backwards motion of gear 604 causes retraction of bolt 408. Pin 618 is urged towards retractor 610 by a spring 620. However, a plurality of inclined planes 621, which are preferably fixed relative to handle 602, meet pin 618 as it moves backwards with linear gear 604 and urge pin 618 away from bolt retractor 610, to a collar retractor 622. Also collar retractor 622 preferably has a plurality of holes 624 formed in it for engaging pin 618. Collar retractor 622 is preferably coupled to collar 404, so that linear motion of gear 604 retracts collar 404. As collar retractor 622 and pin 618 move backwards with linear gear 604, pin 608 moves closer to a hole 614, which, once reached, engages pin 618 and decouples collar retractor 622 from linear gear 604.

Pull-Pull Embodiment

Figure 10B:
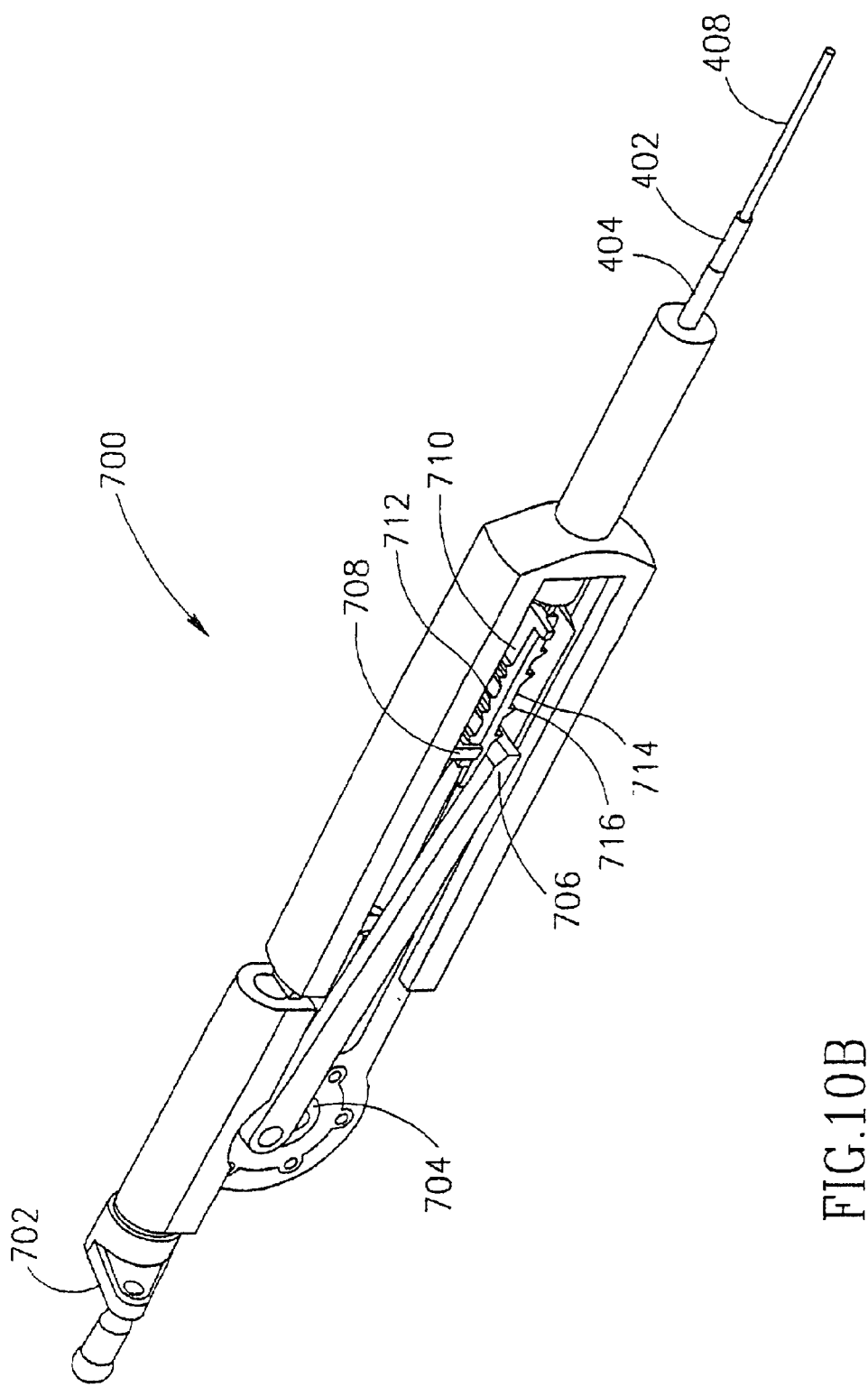

FIGS. 10A–10B illustrate an eccentric-rotation based delivery system 700, in accordance with a preferred embodiment of the invention.

In this embodiment, a knob 702 is used to rotate a wheel 704 (the reference number points to a covering of the wheel, as the rim of the wheel is hidden). Forward motion of the two arms are attached to the wheel, at off-axis positions, such that turning wheel 704 advances one arm and retracts the other arm, for one half of its rotation and retracts the one arm and advances the other arm on its other half of rotation. One arm is a bolt retraction arm 706 and the other arm is a collar retraction arm 708. Each of the arm, when it retracts engages a nubbed bar that is coupled to either collar 404 or bolt 408. When the arms advance, they slip forward, over one or more nubs to the next nub for retraction.

Collar retraction arm 708 engages a nubbed bar 710, having a plurality of one-way nubs 712 formed thereon. Nubs 712 are flat on one side, to engage a flat aperture formed (or protrusion) in arm 708. The nubs are inclined at their other side, to allow an inclined surface of arm 708 to slip over them, when the arm advances.

A similar mechanism is provided for arm 706 and its associated bar 714 and nubs 716.

It is noted that in this and other embodiments, the distance between the nubs (or aperture sin other embodiments) is selected to achieve a desired amount of motion of the collar and/or bolt. Thus, also the retraction motion of the arms may include some slippage of the arm against the bar, rather than retraction. The off-axis assistance between the arm and the wheel axis, can also be used to control the force leveraging and the amount of retraction possible.

In the figures, the bolt, spacer and sleeve are shown extending directly from device 700, however, in some embodiment, a pole element is used for retracting the bolt and/or a spacer pusher is used for coupling the spacer to device 700. In device 700 as shown, the spacer does not move relative to device 700, so device 700 advances as the spacer axially contracts.

Although arms 706 and 708 are shown to be 180° apart from each other, in some embodiment, a different angular difference is used, so that there is an overlap in their advancing and/or retracting motions.

Push-Pull Embodiment

Figure 11:
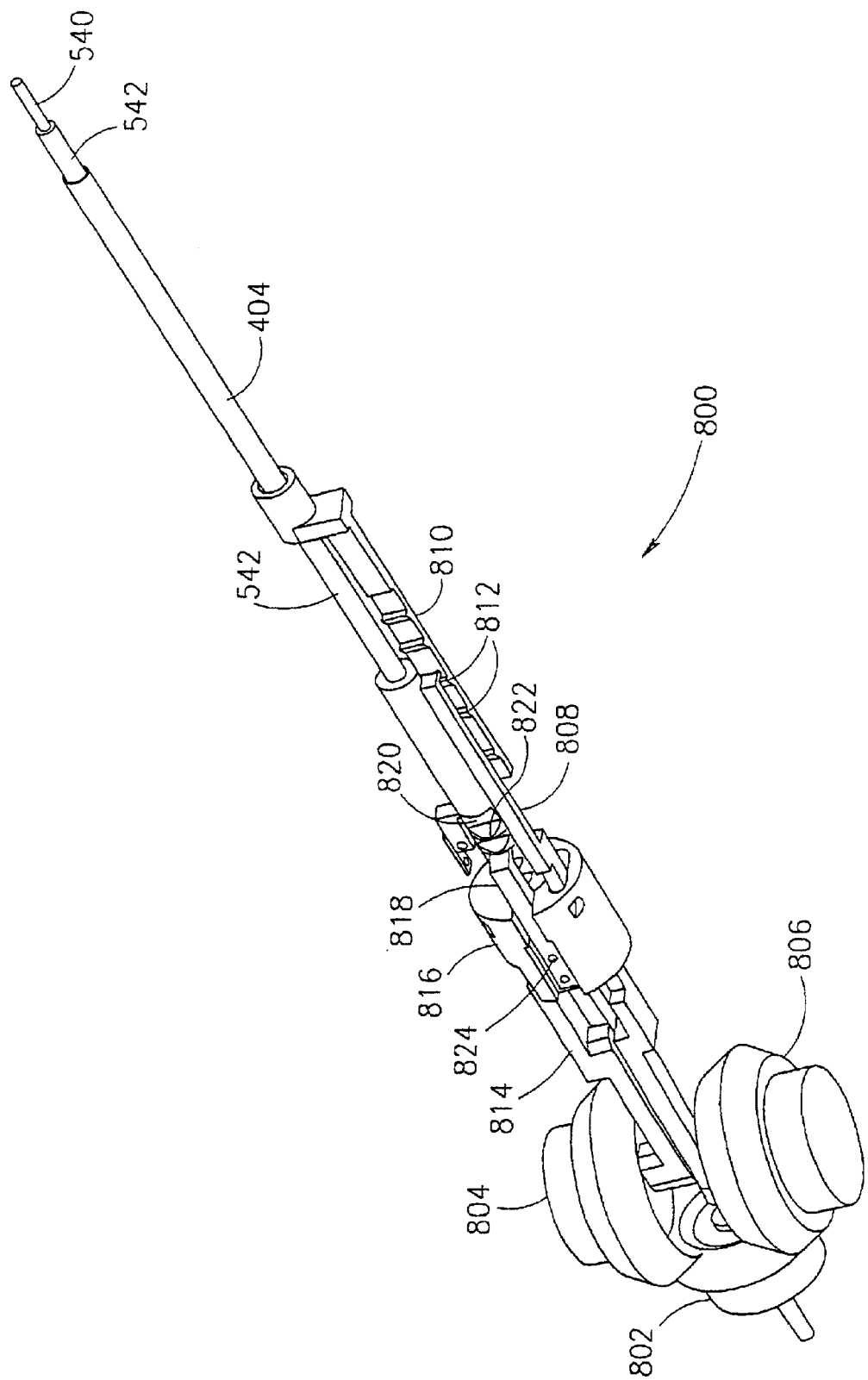
FIG. 11 illustrates an alternative eccentric-rotation based delivery system, in accordance with another preferred embodiment of the invention.

FIG. 11 illustrates an alternative eccentric-rotation based delivery system 800, in accordance with another preferred embodiment of the invention.

System 800 illustrates two features desirable in some preferred embodiments of the invention:

(a) advancing spacer 402 while maintaining bolt 408 in place; and (b) reduction of moments in the forces applied to spacer 402.

These two features are substantially independent and one may be provided without the other.

As will be seen from FIG. 11 and the following description, forces on spacer 402, which are generally the highest forces applied during spacer deployment, are applied substantially axially, so that there is little or no twisting and/or bending moment. In some cases, forces of 30, 60 or even 100 Kg may be applied to the spacer, to expand it.

Like system 700 of FIGS. 10A and 10B, eccentric motion of a wheel is used to alternate advancing and retraction of arms. However, unlike system 700, in system 800, one arm is active while advancing and the other while retracting.

A knob 802 is used to rotate a wheel 804 and a wheel 806. In some embodiments, these wheels include a gear reduction mechanism for reducing motion while increasing force.

Wheel 806 is coupled to an arm 808 which engages a nubbed bar 810 when it retracts, thereby retracting collar 404. As in system 700, when arm 808 advances, it can slip over one or more one-way nubs 812. It should be noted that arm 808 is preferably near the axis of device 800.

Wheel 804 is coupled to an arm 814 which is, in turn, coupled to a cylinder 816 that is centered on the axis of device 800. A nub engaging tip 818 is coupled to cylinder 816, preferably using a leaf spring 824, so that it can engage a nub 822 of a nubbed bar 820, when it advances. When arm 814 retracts, also tip 818 retracts and slips over the one-way nubs, as in system 700.

Although FIG. 11 does not show a sheath. System 800 is preferably sheathed using a cylindrical sheath.

Spacer Removal

Although the spacers are generally permanently implanted, it is sometimes desirable to remove them. In a preferred embodiment of the invention, the same devices used for implanting the spacers are used for retrieving them, being activated backwards (the collar advancing and the spacer retracting or the bolt advancing). Using dedicated devices is useful for controlling the direction in which the spacer will axially grow and to ensure that the uncollapsed spikes do not scratch the surrounding tissue. In some cases, it is necessary to unlock the bolt from the spacer end, for example by cutting or by bending in a flange of the bolt.

Delivery System Fixation

In a preferred embodiment of the invention, the delivery system is hand-held, being fixed in two dimensions by a laproscopic tube used to access space 55. The delivery system may also be fixed to the tube to prevent axial motion and/or rotation. Generally, it is desirable that the system needs to be held with at most one hand (or no hands), leaving a second hand for performing various activities. In some cases, the free hand is used to rotate the knows used to expand the spacer.

In some embodiments, the body of the delivery system is fixed to the patient's body (possibly via a framework) and/or to the bed on which the patient lies. Many fixing methods can be used, for example the delivery system being clamped to the bed. Alternatively, other fixing methods, for example as used in neurological procedures, may be used.

In some embodiments, the operator's hand is not mechanically coupled to the delivery system, for example the delivery system being controlled using a flexible tube or wire or using wireless means.

In any of the above embodiments, power for expanding the spacer may be provided by a motor, rather than from the operator. however, in many cases it is desirable to provide feedback, especially tactile feedback, to the operator regarding the expansion of the spacer. In a preferred embodiment of the invention, non-tactile feedback is provided by a sensor that measures the relative motion of the bolt and the spacer or a sensor that measures the forces applied top the spacer. In a preferred embodiment of the invention, if the forces exceed a threshold, do not match the motion and/or do not match an expected force pattern or if the motion is unusual, an alert is provided, for example an audio alert.

Location Control

In the embodiments described above, a rigid tube is used to control the trans-axial and/or axial location of the delivery system and the spacer and a body stopper is used to limit the axial motion of the spacer. However, in some embodiments, such control may not be suitable or sufficient. In a preferred embodiment of the invention, the implantation of tubes uses x-ray imaging or other external medical imaging techniques to prevent damage to nerves, blood vessels and other adjacent tissue. Alternatively, visual imaging, such as using an endoscope, is used. Alternatively or additionally, ultrasonic imaging is used. Alternatively or additionally, local MRI imaging, for example using a local coil (possibly inside the body) is used. Such imaging tool may be provided through the access tube and through the delivery system, beside the delivery system or instead of the delivery system. In some cases, a second tube with the imaging tool is provided. Alternatively or additionally, a position sensor may be coupled to the tools and using a reference coupled to the body, a position of the tool and/or proximity to various body structures can be determined. Such a display is known in the art and can be overlaid on a two or three dimensional image of the body.

A position sensor or an ultrasonic imager may be integrated with the bolt of the spacer. Alternatively, such a bolt is hollow or is not needed. Space 55 is generally free, so a simple ultrasonic distance sensor may be used to detect if a tool is nearing dangerous areas. Possibly, a Doppler signal is used to detect the proximity of blood vessels. Such a Doppler signal can be time gated.

Alternatively, a fixed framework to which all tools are coupled is used. The allowed motion of the tools relative to the framework can be fixed mechanically or a sensor can detect the motion and generate a signal if an allowed ball park is exceeded.

Although the above described sleeve 102 can serve as such a framework, it is useful if the delivery system is coupled to the sleeve end inside the body and that sleeve 102 can be fixed in place in the body, for example using an expanding tip or a barbed tip. In one embodiment, the collar is threaded to sleeve 102 and retracted by rotation of the collar. Alternatively or additionally, the delivery system may be so fixed to sleeve 102. Alternatively or additionally, a tool that couples the end of the spacer to sleeve 102 is provided to limit or sense motion of the end of the spacer. As the spacer is not solid, this limiting tool can remain in the body while the spacer is being expanded.

The use of an internal reference is especially useful if one or more of the tools is bent or flexible.

Non-Axial Variations

As described above, the various tools are generally rigid and straight. However, in some embodiments of the invention, bent tools, such as tubes and delivery systems, may be used. Alternatively or additionally, flexible tools, tubes and delivery systems may be used.

It is noted that although the above described devices are preferably applied inside the body, at least for testing and training purposes, these devices may also be used to expand an implant outside of a living human body, for example in the air, in a model, in an animal or inside a cadaver.

It will be appreciated that the above described apparatus and methods for delivering expandable inserts may be varied in many ways. In addition, a multiplicity of various features, both of methods and of devices have been described. It should be appreciated that different features may be combined in different ways. In particular, not all the features shown above in a particular embodiment are necessary in every similar preferred embodiment of the invention. Further, combinations of the above features are also considered to be within the scope of some preferred embodiments of the invention. It should also be appreciated that many of the embodiments are described only as methods or only as apparatus, however the scope of the invention includes both methods for using apparatus and apparatus for applying the methods. The scope of the invention also covers machines for creating the apparatus described herein. In addition, the scope of the invention includes methods of using, constructing, calibrating and/or maintaining the apparatus described herein. Section headings where they appear are meant for clarity and ease of browsing the application and are not to be construed as limiting the applicability of subject matter described within. When used in the following claims or in the text above, the terms "comprises", "comprising", "includes", "including" or the like mean "including but not limited to".

What is claimed is:

1. Apparatus for controlling the deformation of an implant during deployment thereof, comprising:
   a force application mechanism for applying deforming force to the implant, by axial motion of a force applicator against the implant; and
   a restraint element positioning mechanism that positions a restraining element such that the deformation of the implant is controlled by restraint of the restraining element on allowable deformation; and
   a synchronizer that synchronizers the motion of the restraining element and the force applicator, to achieve a desired deformation of the implant.

2. Apparatus according to claim 1, comprising a force input which receives continuous motion and couples it to the force application mechanism and to the restraint element positioning mechanism.

3. Apparatus according to claim 2, wherein said continuous motion is reciprocating motion.

4. Apparatus according to claim 3, wherein said restraint positioning mechanism moves said restraint element during one stroke of said reciprocating motion.

5. Apparatus according to claim 4, wherein said one stroke comprises a retraction of said restraint mechanism from said implant.

6. Apparatus according to claim 3, wherein said force application mechanism moves said force applicator during one stroke of said reciprocating motion.

7. Apparatus according to claim 6, wherein said one stroke comprises a retraction of said force applicator from said implant.

8. Apparatus according to claim 6, wherein said one stroke comprises an advance of said force applicator towards said implant.

9. Apparatus according to claim 2, wherein said force application mechanism comprises a selective coupler that selectively couples said input motion to said force applicator.

10. Apparatus according to claim 2, wherein said element positioning mechanism comprises a selective coupler that selectively couples said input motion to said restraining element.

11. Apparatus according to claim 2, wherein said synchronized motion is repetitive, comprises a plurality of cycles of positioning said restraining element and applying said force.

12. Apparatus according to claim 2, wherein said motion is applied simultaneously to said restraint element positioning mechanism and to said force application mechanism.

13. Apparatus according to claim 2, wherein said motion is applied alternately to said restraint element positioning mechanism and to said force application mechanism.

14. Apparatus according to claim 13, comprising an alternating locking mechanism that alternately couples the motion form the force input to the restraint element positioning mechanism and to the force application mechanism.

15. Apparatus according to claim 2, wherein said force input comprises a manual force input.

16. Apparatus according to claim 2, wherein said force input comprises a motorized force input.

17. Apparatus according to claim 1, wherein said synchronizer is integrated with said mechanisms.

18. Apparatus according to claim 1, wherein said synchronizer is manual, providing an indication to an operator to switch between the mechanisms.

19. Apparatus according to claim 1, wherein said synchronizer is automatic, switching by itself between the mechanisms.

20. Apparatus according to claim 1, wherein said synchronizer comprises a pin extractor for decoupling a pin from one mechanism and coupling the pin to another mechanism.

21. Apparatus according to claim 20, wherein said synchronizer comprises a spring for urging said pin towards one of said mechanisms and an inclined plane for withdrawing said pin from said one mechanism and urging said pin towards said other mechanism.

22. Apparatus according to claim 1, wherein said synchronizer blocks the motion of one of said mechanisms when a desired motion effect of said mechanism is achieved.

23. Apparatus according to claim 22, comprising a pin that engages an aperture to effect said locking.

24. Apparatus according to claim 1, wherein said restraint mechanism comprises an unevenly surfaced element for coupling said motion to said restraint element.

25. Apparatus according to claim 1, wherein said force application mechanism comprises an unevenly surfaced element for coupling said motion to said force applicator.

26. Apparatus according to claim 24, wherein said unevenly surfaced element comprises a nubbed plate.

27. Apparatus according to claim 26, wherein said nubs are one-way nubs that allow an arm element of said mechanisms to slip over them when the arm travels in one direction relative to the nubs and engages the arm when the arm travels in the opposite relative direction.

28. Apparatus according to claim 24, wherein said unevenly surfaced element comprises an apertured plate.

29. Apparatus according to claim 24, wherein said uneven surface comprises even surface portions separated, by uneven surface portions, a plurality of separation distances defined by said separation of surface portions.

30. Apparatus according to claim 29, wherein said separation distances determine the deformation of said implant.

31. Apparatus according to claim 29, wherein said separation distances take into account a plastic deformation of said implant.

32. Apparatus according to claim 29, wherein said separation distances take into account an elastic deformation of said implant.

33. Apparatus according to claim 29, wherein said separation distances take into account a spring-back of said implant.

34. Apparatus according to claim 1, wherein said force applicator and said force application mechanism are substantially restricted to a straight, narrow, elongate volume, thereby reducing moments on the force application mechanism.

35. Apparatus according to claim 1, wherein said force applicator pushes against said implant.

36. Apparatus according to claim 1, wherein said force applicator pulls a base against a far side of said implant.

37. Apparatus according to claim 1, wherein said force applicator exhibits axial motion, along an axis connecting the force applicator and the implant.

38. Apparatus according to claim 1, wherein said force applicator exhibits rotational motion, around an axis connecting the force applicator and the implant.

39. Apparatus according to claim 37, wherein said force applicator exhibits only axial motion, along an axis connecting the force applicator a nd the implant.

40. Apparatus according to claim 1, wherein said restraint element exhibits axial motion, along an axis connecting the force applicator and the implant.

41. Apparatus according to claim 1, wherein said restraint element exhibits rotational motion, around an axis connecting the force applicator and the implant.

42. Apparatus according to claim 40, wherein said force applicator exhibits only axial motion, during times when force is applied by it to the implant, along an axis connecting the force applicator and the implant.

43. Apparatus according to claim 1, wherein said force applicator applies at least 20 Kg to said implant.

44. Apparatus according to claim 1, wherein said force applicator applies at least 40 Kg to said implant.

45. Apparatus according to claim 1, wherein said force applicator applies at least 60 Kg to said implant.

46. Apparatus according to claim 1, wherein said force applicator applies at least 100 Kg to said implant.

47. Apparatus according to claim 1, wherein said restraint element and said force applicator are elongate elements.

48. Apparatus according to claim 47, wherein said restraint element and said force applicator are cylindrical elements.

49. Apparatus according to claim 47, wherein said cylindrical elements are tubes.

50. Apparatus according to claim 1, wherein said force applicator comprises two concentric elements, an outer element which applies force away from said apparatus towards said implant and an inner counter force element that applies force from said implant towards said apparatus.

51. Apparatus according to claim 50, wherein said inner element is mechanically coupled to said implant.

52. Apparatus according to claim 50, wherein said outer element is mechanically coupled to said implant.

53. Apparatus according to claim 50, wherein said motion of said force applicator comprises motion of only one of said concentric elements relative to said apparatus.

54. Apparatus according to claim 53, wherein said inner element retracts towards said apparatus during said motion of said force applicator.

55. Apparatus according to claim 53, wherein said outer element advances away from said apparatus during said motion of said force applicator.

56. Apparatus according to claim 50, wherein said inner element is decoupled from said implant by unscrewing it.

57. Apparatus according to claim 56, wherein said inner element extends substantially all the way through said apparatus.

58. Apparatus according to claim 1, comprising a handle for holding said apparatus by an operator.

59. Apparatus according to claim 1, comprising means for fixing said apparatus to said patient.

60. Apparatus according to claim 1, comprising means for fixing said apparatus to a bed on which said patient lies.

61. Apparatus according to claim 1, wherein said synchronizer adapts said apparatus for deforming a particular implant from a set of same types of implants having different geometries.

62. Apparatus according to claim 1, wherein said synchronizer synchronizes said force applicator to apply force to said implant after said implant is completely expanded.

63. Apparatus according to claim 1 wherein said restraint element has an outer diameter of less than 7 mm.

64. Apparatus according to claim 1 wherein said restraint element has an outer diameter of less than 6 mm.

65. Apparatus according to claim 1 wherein said restraint element has an outer diameter of less than 5 mm.

66. Apparatus according to claim 1 wherein said restraint element has an outer diameter of less than 4 mm.

67. Apparatus according to claim 1, wherein said implant is a spinal implant for fusing adjacent vertebrae.

68. Apparatus according to claim 1, wherein said implant is an axially contracting and radially expanding implant.

69. Apparatus according to claim 1, wherein said implant comprises a slotted tube, which as it contracts, radially extends a plurality of spikes and wherein said restraining element encloses said tube and prevents the extension of at least one of said spikes.

70. Apparatus according to claim 1, wherein said implant comprises a slotted tube, to which force is applied against an end of said tube, to deform the tube.

71. Apparatus according to claim 1, wherein said implant radially expands by said deforming at least by a ratio of two.

72. Apparatus according to claim 1 wherein said implant radially expands by said deforming at least by a ratio of four.

73. A method of controlling the deformation of an implant, comprising:

providing a medical implant;

positioning a restraining element relative to said implant, which restraining element prevents deformation of at least some of said implant;

applying a deformation force to said implant using at least one tube;

controlling the deformation of the implant using the restraining element;

moving said restraining element to a new position; and repeating said applying, said controlling and said moving, a plurality of times, such that in each repetition a different portion of the implant is prevented from deforming by the restraining element.

74. A method according to claim 73, wherein said deformation comprises radial expansion.

75. A method according to claim 73, wherein said restraining element is inside said implant.

76. A method according to claim 73, wherein said restraining element is outside said implant.

77. A method according to claim 73, wherein said motion of said restraining element is controlled using a mechanism external to the implant.

78. A method according to claim 77, wherein said external mechanism receives a continuous motion input from an operator.

79. A method according to claim 78, comprising converting said continuous motion into discrete motion of said restraining element.

80. A method according to claim 78, comprising converting said continuous motion into discrete application of force to said implant.

81. A method according to claim 73, wherein said motion and said force application do not overlap in time.

82. A method according to claim 73, wherein said motion and said force application do overlap in time.

83. A method of controlling the deformation of an implant, composing:
- providing an axial implant having a plurality of spikes extending radially thereto, arranged along the implant's axis, which implant is in a collapsed state where said spikes do not extend;
- enclosing said implant with a collar that restrains the extension of said spikes;
- inserting said implant into a desired location;
- retracting said collar to allow at least one spike to extend; and
- repeating said retracting until substantially all of said spikes are extended.

84. A method according to claim 83, wherein said spikes extend as a result of forces stored within said implant.

85. A method according to claim 84, wherein said implant is formed of a super-elastic material.

86. A method according to claim 84, wherein said implant is formed of a shape-memory material.

87. A method according to claim 83, wherein said spikes extend as a result of forces applied externally to said implant.

88. A method according to claim 87, wherein said forces are axially applied to said implant.

89. A method according to claim 88, comprising applying an axial force to said implant after all of said spikes are extended.

90. Apparatus for controlling the deformation of a tube having a slotted section, comprising:
- a force application mechanism for applying deforming force to the slotted section, by axial motion of a force applicator against the slotted section;
- a restraint element positioning mechanism that positions a restraining element such that the deformation of the slotted section is controlled by restraint of the restraining element on allowable deformation; and
- a synchronizer that synchronizers the motion of the restraining element and the force applicator, to achieve a desired deformation of the slotted section.

91. An apparatus according to claim 90, wherein said slotted section is formed of plastic.

92. Apparatus according to claim 90, comprising a force input which receives continuous motion and couples it to the force application mechanism and to the restraint element positioning mechanism.

93. Apparatus according to claim 92, wherein said continious motion is reciprocating motion.

94. Apparatus according to claim 93, wherein said restraint positioning mechanism moves said restraint element during one stroke of said reciprocating motion.

95. Apparatus according to claim 94, wherein said one stroke comprises a retraction of said restraint mechanism from said slotted section.

96. Apparatus according to claim 93, wherein said force application mechanism moves said force applicator during one stroke of said reciprocating motion.

97. Appratus according to claim 96, wherein said one stroke comprises a refraction of said force applicator from said slotted section.

98. Apparatus according to claim 96, wherein said one stroke comprises an advance of said force applicator towards said slolled section.

99. Apparatus according to claim 92, wherein said force application mechanism comprises a selective coupler that selectively couples said input motion to said force applicator.

100. Apparatus according to claim 92, wherein said element positioning mechanism comprises a selective coupler that selectively couples said input motion to said restraining element.

101. Apparatus according to claim 92, wherein said synchronized motion is repetitive and comprises a plurality of cycles of positioning said restraining element and applying said force.

102. Apparatus according to claim 92, wherein said motion is applied simultaneously to said restraint element positioning mechanism and to said force application mechanism.

103. Apparatus according to claim 92, wherein said motion is applied alternately to said restraint element positioning mechanism and to said force application mechanism.

104. Apparatus according to claim 103, comprising an alternating locking mechanism that alternately couples the motion from the force input to the restraint element positioning mechanism and to the force application mechanism.

105. Apparatus according to claim 92, wherein said force input comprises a manual force input.

106. Apparatus according to claim 92, wherein said force input comprises a motorized force input.

107. Apparatus according to claim 90, wherein said synchronizer is integrated with said mechanisms.

108. Apparatus according to claim 90, wherein said synchronizer is manual, providing an indication to an operator to switch between the mechanisms.

109. Apparatus according to claim 90, wherein said synchronizer is automatic, switching by itself between the mechanisms.

110. Apparatus according to claim 90, wherein said synchronizer comprises a pin extractor for decoupling a pm from one mechanism and coupling the pin to another mechanism.

111. Apparatus according to claim 110, wherein said synchronizer comprises a spring for urging said pin towards one of said mechanisms and an inclined plane for withdrawing said pin from said one mechanism and urging said pin towards said other mechanism.

112. Apparatus according to claim 90, wherein said synchronizer blocks the motion of one of said mechanisms when a desired motion effect of said mechanism is achieved.

113. Apparatus according to claim 112, comprising a pin that engages an aperture to effect said locking.

114. Apparatus according to claim 90, wherein said restraint mechanism comprises an unevenly surfaced element for coupling said motion to said restraint element.

115. Appratus according to claim 90, wherein said force application mechanism comprises an unevenly surfaced element for coupling said motion to said force applicator.

116. Apparatus according to claim 114, wherein said unevenly surfaced element comprises a nubbed plate.

117. Apparatus according to claim 116, wherein said nubs are one-way nubs that allow an arm element of said mechanisms to slip over them when the arm travels in one direction relative to the nubs and engages the arm when the aim travels in the opposite relative direction.

118. Apparatus according to claim 114, wherein said unevenly surfaced element comprises an apertured plate.

119. Apparatus according to claim 114, wherein said uneven surface comprises even surface portions separated, by uneven surface portions, a plurality of separation distances defined by said separation of surface portions.

120. Apparatus according to claim 119, wherein said separation distances determine the deformation of said slotted section.

121. Appratus according to claim 119, wherein said separation distances take into account a plastic deformation of said slotted section.

122. Apparatus according to claim 119, wherein said separation distances take into account an elastic deformation of said slotted section.

123. Apparatus according to claim 119, wherein said separation distances take into account a spring-back of said slotted section.

124. Apparatus according to claim 90, wherein said force applicator and said force application mechanism are substantially restricted to a straight, narrow, elongate volume, thereby reducing moments on the force application mechanism.

125. Apparatus according to claim 90, wherein said force applicator pushes against said slotted section.

126. Apparatus according to claim 90, wherein said force applicator pulls a base against a far side of said slotted section.

127. Apparatus according to claim 90, wherein said force applicator exhibits axial motion, along an axis connecting the force applicator and the slotted section.

128. Apparatus according to claim 90, wherein said force applicator exhibits rotational motion, around an axis connecting the force applicator and the slotted section.

129. Apparatud according to claim 127, wherein said force applicator exhibits only axial motion, along an axis connecting the force applicator and the slotted section.

130. Apparatus according to claim 90, wherein said restraint element exhibits axial motion, along an axis connecting the force applicator and the slotted section.

131. Apparatus according to claim 90, wherein said restraint element exhibits rotational motion, around an axis connecting the force applicator and the slotted section.

132. Apparatus according to claim 130, wherein said force applicator exhibits only axial motion, during times when force is applied by it to the slotted section, along an axis connecting the force applicator and the slotted section.

133. Apparatus according to claim 90, wherein said force applicator applies at least 20 Kg to said slotted section.

134. Apparatus according to claim 90, wherein said force applicator applies at least 40 Kg to said slotted section.

135. Apparatus according to claim 90, wherein said force applicator applies at least 60 Kg to said slotted section.

136. Apparatus according to claim 90, wherein said force applicator applies at least 100 Kg to said slotted section.

137. Apparatus according to claim 90, wherein said restraint element and said force applicator are elongate elements.

138. Apparatus according to claim 137, wherein said restraint element and said force applicator are cylindrical elements.

139. Apparatus according to claim 137, wherein said cylindrical elements are tubes.

140. Apparatus according to claim 90, wherein said force applicator comprises two concentric elements, an outer element which applies force away from said apparatus towards said slotted section and an inner counter force element that applies force from said slotted section towards said apparatus.

141. Apparatus according to claim 140, wherein said inner element is mechanically coupled to said slotted section.

142. Apparatus according to claim 140, wherein said outer element is mechanically coupled to said slotted section.

143. Apparatus according to claim 140, wherein said motion of said force applicator comprises motion of only one of said concentric elements relative to said apparatus.

144. Apparatus according to claim 143, wherein said inner element retracts towards during said motion of said force applicator.

145. Apparatus according to claim 143, wherein said outer element advances away from said apparatus during said motion of said force applicator.

146. Apparatus according to claim 140, wherein said inner element extends substantially all the way through said apparatus.

147. Apparatus according to claim 90, comprising a handle for holding said apparatus by an operator.

148. Apparatus according to claim 90, comprising means for fixing said apparatus to said patient.

149. Apparatus according to claim 90, comprising means for fixing said apparatus to a bed on which said patient lies.

150. Apparatus according to claim 90, wherein said synchronizer synchronizes said force applicator to apply force to said slotted section after said slotted section is completely expanded.

151. Apparatus according to claim 90 wherein said restraint element has an outer diameter of less than 7 mm.

152. Apparatus according to claim 90 wherein said restraint element has an outer diameter of less than 6 mm.

153. Apparatus according to claim 90 wherein said restraint element has an outer diameter of less than 5 mm.

154. Apparatus according to claim 90 wherein said restraint element has an outer diameter of less than 4 mm.

155. Apparatus according to claim 90 wherein said slotted section radially expands by said deforming at least by a ratio of two.

156. Apparatus according to claim 90 wherein said slotted section radially expands by said deforrning at least by a ratio of four.

157. Apparatus according to claim 147, wherein said apparatus is configured that a distal end of said slotted section does not move relative to said handle during said applying.

158. Apparatus according to claim 58, wherein said apparatus is configured so that a distal end of said implant does not move relative to said handle during said applying.

159. Apparatus according to claim 90, wherein said slotted section is configured to expand to have a uniform radial diameter.

160. Apparatus according to claim 90, wherein said slotted section is configured to expand to have a radial diameter which varies along the tube axis.

161. Apparatus according to claim 90, wherein said slotted section comprises an end portion of an unslotted tube.

162. A method of controlling the deformation of a slotted tube, comprising:
  providing an axial tube having at least a slotted end such that said slots are configured to expand as a plurality of spikes extending radially thereto, said spikes arranged along the tube axis, which slotted end is in a collapsed state where said spikes do not extend;
  enclosing said slotted end with a collar that restrains the extension of said spikes;
  inserting said tube into solid tissue;
  retracting said collar relative to said slotted end to allow at least one spike to extend in said solid tissue; and
  repeating said retracting until substantially all of said spikes are extended.

163. A method according to claim 162, wherein said slotted tube is formed of plastic.

* * * * *